(12) United States Patent
Cho et al.

(10) Patent No.: US 7,723,319 B2
(45) Date of Patent: May 25, 2010

(54) ACYCLIC NUCLEOSIDE PHOSPHONATE DERIVATIVES, SALTS THEREOF AND PROCESS FOR THE PREPARATION OF THE SAME

(75) Inventors: Dong-Gyu Cho, Taejeon (KR); Jae-Hong Lim, Taejeon (KR); Jae-Taeg Hwang, Taejeon (KR); Woo-Young Cho, Taejeon (KR); Hyun-Sook Jang, Taejeon (KR); Chang-Ho Lee, Taejeon (KR); Tae-Saeng Choi, Taejeon (KR); Chung-Mi Kim, Taejeon (KR); Yong-Zu Kim, Taejeon (KR); Tae-Kyun Kim, Taejeon (KR); Seung-Joo Cho, Taejeon (KR); Gyoung-Won Kim, Taejeon (KR); Jong-Ryoo Choi, Taejeon (KR); Jeong-Min Kim, Taejeon (KR); Kee-Yoon Roh, Taejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 12/585,229

(22) Filed: Sep. 9, 2009

(65) Prior Publication Data

US 2010/0004440 A1 Jan. 7, 2010

Related U.S. Application Data

(60) Division of application No. 11/455,679, filed on Jun. 20, 2006, now Pat. No. 7,605,147, which is a continuation-in-part of application No. 10/450,780, filed as application No. PCT/KR02/00086 on Jan. 18, 2002, now Pat. No. 7,157,448.

(30) Foreign Application Priority Data

Jan. 19, 2001 (KR) ................................ 2001-3087

(51) Int. Cl.
C07F 9/6561 (2006.01)
C07F 9/6512 (2006.01)
C07F 9/40 (2006.01)
A61K 31/675 (2006.01)
A61P 31/20 (2006.01)

(52) U.S. Cl. ................ 514/81; 544/118; 544/244; 544/243; 558/189; 536/26.1; 536/25.34

(58) Field of Classification Search ................... None
See application file for complete search history.

(56) References Cited

U.S. PATENT DOCUMENTS

| | | | |
|---|---|---|---|
| 4,039,654 A * | 8/1977 | Walker ........................ 514/530 |
| 5,663,159 A | 9/1997 | Starrett, Jr. et al. |
| 5,688,778 A | 11/1997 | Kim et al. |
| 5,693,798 A | 12/1997 | Kim et al. |
| 5,792,756 A | 8/1998 | Starrett, Jr. et al. |
| 5,817,647 A | 10/1998 | Casara et al. |
| 5,837,871 A | 11/1998 | Kim et al. |
| 5,877,166 A | 3/1999 | Reist et al. |
| 5,886,179 A | 3/1999 | Arimilli et al. |
| 5,935,946 A | 8/1999 | Munger, Jr. et al. |
| 5,977,061 A | 11/1999 | Holy et al. |
| 6,037,335 A | 3/2000 | Takashima et al. |
| 6,069,249 A | 5/2000 | Arimilli et al. |
| 7,157,448 B2 | 1/2007 | Choi et al. |
| 2005/0124582 A1 | 6/2005 | Zemlicka et al. |

FOREIGN PATENT DOCUMENTS

| | | |
|---|---|---|
| EP | 420559 | 9/1990 |
| WO | WO-95/22330 | 8/1995 |
| WO | WO-96/09307 | 3/1996 |
| WO | WO-99/09031 | 2/1999 |
| WO | WO-02/057288 A1 | 7/2002 |
| WO | WO-2004/029064 A1 | 4/2004 |

OTHER PUBLICATIONS

De Clercq, Erik, International Journal of Antimicrobial Agents, 1999, pp. 81-95, vol. 12.
De Clercq, Erik et al., Nature, Oct. 2, 1986, pp. 464-467, vol. 323.
Kim, Un Choung et al., Heterocycles, Nov. 9, 1990, pp. 1571-1574, vol. 31.
Holy, Anonin et al., J. Med. Chem., 1999, pp. 2064-2086, vol. 42.
Zemlicka, Jiri, Pharmacology & Therapeutics, 2000, pp. 251-266, 85.
Yokota, T. et al., Antiviral Chemistry & Chemotherapy, 1994, pp. 57-63, vol. 5(2).
Perni, Robert B. et al., Bioorganic & Medicinal Chemistry Letter 10, 2000, pp. 2687-2690.
Krejcova, Romana et al., Biochemical Pharmacology, 2000, pp. 1907-1913, vol. 60.
Arimilli, MN et al., Antiviral Chemistry & Chemotherapy, 1997, pp. 557-564, vol. 8/7.
Neyts, J. et al., Antimicrobial Agents and Chemotherapy, 1999, pp. 2885-2892, vol. 43, No. 12.
Denis, J.M. et al., Phosphorous, Sulfur, and Silicon, 1990, pp. 317-320, vols. 49/50.
"Basic Mathematic Symbols" http://encyclopedia.laborlawtalk.com/mathematical_symbol downloaded from the Internet May 9, 2005.
Phosphorous Sulfur, 1990, pp. 313-321, vol. 3, No. 3.
Guan, Hui-Ping, Tetrahedron, Jul. 22, 2002, pp. 6047-6059, vol. 58, Issue 30.

* cited by examiner

*Primary Examiner*—Kamal A Saeed
*Assistant Examiner*—Michael Barker
(74) *Attorney, Agent, or Firm*—Birch, Stewart, Kolasch & Birch, LLP

(57) ABSTRACT

The present invention relates to an acyclic nucleoside phosphonate derivative which is useful as an antiviral agent (particularly, against hepatitis B virus), pharmaceutically acceptable salts, stereoisomers, and a process for the preparation thereof.

1 Claim, No Drawings

ACYCLIC NUCLEOSIDE PHOSPHONATE DERIVATIVES, SALTS THEREOF AND PROCESS FOR THE PREPARATION OF THE SAME

This Application is a Divisional of application Ser. No. 11/455,679, filed on Jun. 20, 2006, now U.S. Pat. No. 7,605,147 which is a continuation-in-part (CIP) of U.S. application Ser. No. 10/450,780, filed Jun. 18, 2003 now U.S. Pat. No. 7,157,448, which application Ser. No. 10/450,780 is the U.S. National Phase of PCT International Application No. PCT/KR2002/00086 filed on Jan. 18, 2002 under 35 U.S.C. §371. Priority is also claimed to Korean Application No. 2001-3087 filed on Jan. 19, 2001 in Korea. The entire contents of each of the above-identified applications are hereby incorporated by reference.

TECHNICAL FIELD

The present invention relates to an acyclic nucleoside phosphonate derivative represented by the following formula (1):

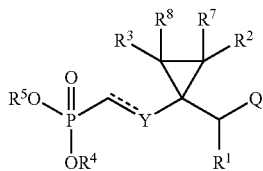

(1)

in which

----- represents single bond or double bond, $R^1$, $R^2$, $R^3$, $R^7$ and $R^8$ independently of one another represent hydrogen, halogen, hydroxy, amino, $C_1$-$C_7$-alkyl, $C_2$-$C_6$-alkenyl, $C_1$-$C_5$-alkylamino, $C_1$-$C_5$-aminoalkyl, or $C_1$-$C_5$-alkoxy, $R^4$ and $R^5$ independently of one another represent hydrogen, or represent $C_1$-$C_4$-alkyl optionally substituted by one or more substituents selected from the group consisting of halogen (particularly, fluorine), $C_1$-$C_4$-alkoxy, phenoxy, $C_7$-$C_{10}$-phenylalkoxy and $C_2$-$C_5$-acyloxy, or represent $C_1$-$C_7$-acyl, $C_6$-$C_{12}$-aryl or optionally substituted carbamoyl, or represent —(CH$_2$)m-OC(═O)—$R^6$ wherein m denotes an integer of 1 to 12 and $R^6$ represents $C_1$-$C_{12}$-alkyl, $C_2$-$C_7$-alkenyl, $C_1$-$C_5$-alkoxy, $C_1$-$C_7$-alkylamino, di($C_1$-$C_7$-alkyl)amino, $C_3$-$C_6$-cycloalkyl, or 3 to 6-membered heterocycle having 1 or 2 hetero atoms selected from a group consisting of nitrogen and oxygen, Y represents —O—, —S—, —CH(Z)—, ═C(Z)—, —N(Z)—, ═N—, —SiH(Z)—, or ═Si(Z)—, wherein Z represents hydrogen, hydroxy or halogen, or represents $C_1$-$C_7$-alkyl, $C_1$-$C_5$-alkoxy, allyl, hydroxy-$C_1$-$C_7$-alkyl, $C_1$-$C_7$-aminoalkyl or phenyl, Q represents a group having the following formula:

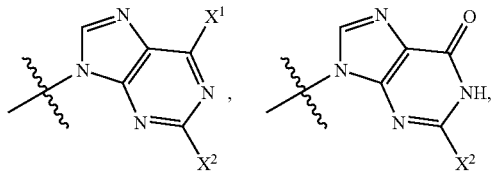

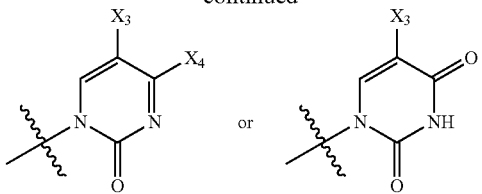

wherein $X^1$, $X^2$, $X^3$ and $X^4$ independently of one another represent hydrogen, amino, hydroxy or halogen, or represent $C_1$-$C_7$-alkyl, $C_1$-$C_5$-alkoxy, allyl, hydroxy-$C_1$-$C_7$-alkyl, phenyl or phenoxy each of which is optionally substituted by nitro or $C_1$-$C_5$-alkoxy, or represent $C_6$-$C_{10}$-arylthio which is optionally substituted by nitro, amino, $C_1$-$C_6$-alkyl or $C_1$-$C_4$-alkoxy, or represent $C_6$-$C_{12}$-arylamino, $C_1$-$C_7$-alkylamino, di($C_1$-$C_7$-alkyl)amino, $C_3$-$C_6$-cycloalkylamino or a structure of

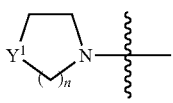

wherein n denotes an integer of 1 or 2 and $Y^1$ represents O, CH$_2$ or N—R (R represents $C_1$-$C_7$-alkyl or $C_6$-$C_{12}$-aryl), which is useful as an antiviral agent (particularly, against hepatitis B virus), pharmaceutically acceptable salts, stereoisomers, and a process for the preparation thereof.

BACKGROUND ART

Purine or pyrimidine derivatives have anti-cancer and antiviral activities, and more than 10 kinds of the compounds including AZT, 3TC and ACV have already been commercialized. Particularly, since acyclic nucleoside phosphonate derivatives show a potent antiviral effect, cidopovir has been commercialized as an antiviral agent and many compounds including PMEA and PMPA now entered into the step of clinical trials. However, the earlier developed compounds were not perfect in the aspects of toxicity or pharmaceutical activity, and thus, it is still desired to develop a compound having no toxicity as well as a superior activity. The prior researches for purine or pyrimidine derivatives or acyclic nucleoside phosphonate derivatives as reported heretofore are as follows. Patents: U.S. Pat. No. 5,817,647; U.S. Pat. No. 5,977,061; U.S. Pat. No. 5,886,179; U.S. Pat. No. 5,837,871; U.S. Pat. No. 6,069,249; WO 99/09031; WO96/09307; WO95/22330; U.S. Pat. No. 5,935,946; U.S. Pat. No. 5,877,166; U.S. Pat. No. 5,792,756; Journals: *International Journal of Antimicrobial Agents* 12 (1999), 81-95; *Nature* 323 (1986), 464; *Heterocycles* 31(1990), 1571; *J. Med. Chem.* 42 (1999), 2064; *Pharmacology & Therapeutics* 85 (2000), 251; *Antiviral Chemistry & Chemotherapy* 5 (1994), 57-63; *Bioorganic & Medicinal Chemistry Letters* 10 (2000) 2687-2690; *Biochemical Pharmacology* 60 (2000), 1907-1913; *Antiviral Chemistry & Chemotherapy* 8 (1997) 557-564; *Antimicrobial Agent and Chemotherapy* 42 (1999) 2885-2892.

DISCLOSURE OF INVENTION

Thus, the present inventors extensively studied to develop a compound having a superior biological activity (pharmaceutical effect) to as well as a lower toxicity than the existing acyclic nucleoside phosphonates commercialized or entered into the step of clinical trials. As a result, we found that the above compound of formula (1) characterized by its unique chemical structure exhibits a potent pharmaceutical activity, and then completed the present invention.

Therefore, one object of the present invention is to provide the compound of formula (1) having a good use of antiviral agent, pharmaceutically acceptable salts or isomers thereof.

It is another object of the present invention to provide a process for the preparation of the compound of formula (1).

It is still another object of the present invention to provide intermediates which are advantageously used for the preparation of the compound of formula (1).

BEST MODE FOR CARRYING OUT THE INVENTION

The compound of formula (1) according to the present invention, as represented below, is a type of acyclic nucleoside phosphonate derivative having a natural base, such as for example, adenine, guanine, uracil, cytosine, thymine or derivatives thereof:

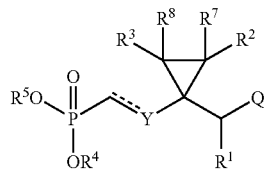

(1)

in which

----- represents single bond or double bond, $R^1$, $R^2$, $R^3$, $R^7$ and $R^8$ independently of one another represent hydrogen, halogen, hydroxy, amino, $C_1$-$C_7$-alkyl, $C_2$-$C_6$-alkenyl, $C_1$-$C_5$-alkylamino, $C_1$-$C_5$-aminoalkyl, or $C_1$-$C_5$-alkoxy, $R^4$ and $R^5$ independently of one another represent hydrogen, or represent $C_1$-$C_4$-alkyl optionally substituted by one or more substituents selected from the group consisting of halogen (particularly, fluorine), $C_1$-$C_4$-alkoxy, phenoxy, $C_7$-$C_{10}$-phenylalkoxy and $C_2$-$C_5$-acyloxy, or represent $C_1$-$C_7$-acyl, $C_6$-$C_{12}$-aryl or optionally substituted carbamoyl, or represent —$(CH_2)$m-OC(=O)—$R^6$ wherein m denotes an integer of 1 to 12 and $R^6$ represents $C_1$-$C_{12}$-alkyl, $C_2$-$C_7$-alkenyl, $C_1$-$C_5$-alkoxy, $C_1$-$C_7$-alkylamino, di($C_1$-$C_7$-alkyl)amino, $C_3$-$C_6$-cycloalkyl, or 3 to 6-membered heterocycle having 1 or 2 hetero atoms selected from a group consisting of nitrogen and oxygen, Y represents —O—, —S—, —CH(Z)—, =C(Z)—, —N(Z)—, =N—, —SiH(Z)—, or =Si(Z)—, wherein Z represents hydrogen, hydroxy or halogen, or represents $C_1$-$C_7$-alkyl, $C_1$-$C_5$-alkoxy, allyl, hydroxy-$C_1$-$C_7$-alkyl, $C_1$-$C_7$-aminoalkyl or phenyl, Q represents a group having the following formula:

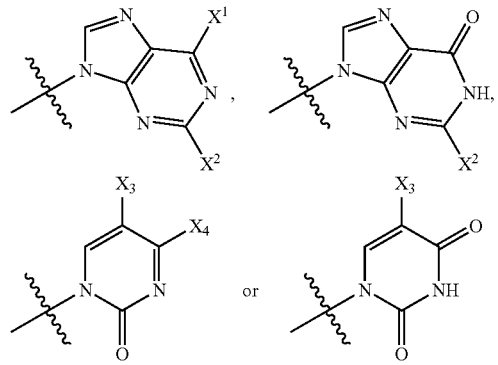

wherein $X^1$, $X^2$, $X^3$ and $X^4$ independently of one another represent hydrogen, amino, hydroxy or halogen, or represent $C_1$-$C_7$-alkyl, $C_1$-$C_5$-alkoxy, allyl, hydroxy-$C_1$-$C_7$-alkyl, phenyl or phenoxy each of which is optionally substituted by nitro or $C_1$-$C_5$-alkoxy, or represent $C_6$-$C_{10}$-arylthio which is optionally substituted by nitro, amino, $C_1$-$C_6$-alkyl or $C_1$-$C_4$-alkoxy, or represent $C_6$-$C_{12}$-arylamino, $C_1$-$C_7$-alkylamino, di($C_1$-$C_7$-alkyl)amino, $C_3$-$C_6$-cycloalkylamino or a structure of

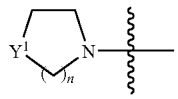

wherein n denotes an integer of 1 or 2 and $Y^1$ represents O, $CH_2$ or N—R (R represents $C_1$-$C_7$-alkyl or $C_6$-$C_{12}$-aryl).

Since the compound of formula (1) according to the present invention may have one or more asymmetric carbon atoms in the structure depending on the kind of substituents, it can be present in the form of the individual enantiomers, diastereomers, or mixtures thereof including racemate. Further, when a double bond is included in the structure, it can be present in the form of E or Z isomer. Thus, the present invention also includes all of these isomers and their mixtures.

Also, the compound of formula (1) according to the present invention can form a pharmaceutically acceptable salt. Such salt includes non-toxic acid addition salt containing pharmaceutically acceptable anion, for example a salt with inorganic acids such as hydrochloric acid, sulfuric acid, nitric acid, phosphoric acid, hydrobromic acid, hydriodic acid, etc., a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, etc., or a salt with sulfonic acids such as methanesulfonic acid, benzenesulfonic acid, p-toluenesulfonic acid, naphthalenesulfonic acid, etc., particularly preferably with sulfuric acid, methanesulfonic acid or hydrohalic acid, etc.

Among the compound of formula (1) showing a potent pharmaceutical activity, the preferred compounds are those wherein ----- represents single bond, $R^1$, $R^2$, $R^3$, $R^7$ and $R^8$ independently of one another represent hydrogen, fluorine, hydroxy, $C_1$-$C_7$-alkyl, $C_2$-$C_6$-alkenyl, $C_1$-$C_5$-alkylamino, $C_1$-$C_5$-aminoalkyl, or $C_1$-$C_5$-alkoxy, $R^4$ and $R^5$ independently of one another represent hydrogen, or represent $C_1$-$C_4$-alkyl optionally substituted by one or more substituents selected from the group consisting of fluorine, $C_1$-$C_4$-alkoxy and phenoxy, or represent carbamoyl substituted by $C_1$-$C_5$-alkyl, or represent —$(CH_2)$m-OC(=O)—$R^6$ wherein m denotes an integer of 1 to 12 and $R^6$ represents $C_1$-$C_{12}$-alkyl, $C_2$-$C_7$-alkenyl, $C_1$-$C_5$-alkoxy, $C_1$-$C_7$-alkylamino, di($C_1$-$C_7$-alkyl)amino, $C_3$-$C_6$-cycloalkyl, or 3 to 6-membered heterocycle having 1 or 2 hetero atoms selected from a group consisting of nitrogen and oxygen, Y represents —O—, —S—, or —N(Z)—, wherein Z represents hydrogen, hydroxy, $C_1$-$C_7$-alkyl, or hydroxy-$C_1$-$C_7$-alkyl, Q represents a group having the following formula:

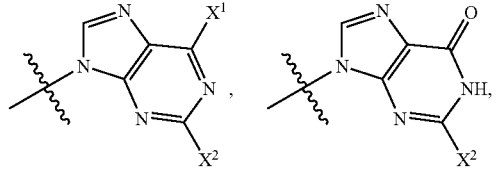

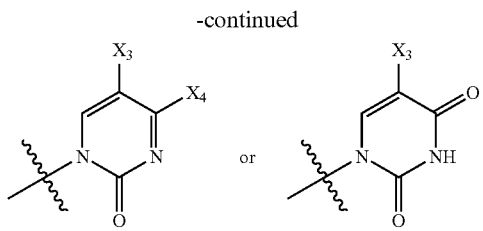

wherein $X^1$ represents hydrogen, amino, hydroxy or halogen, or represents $C_1$-$C_7$-alkyl, $C_1$-$C_5$-alkoxy, hydroxy-$C_1$-$C_7$-alkyl or phenoxy each of which is optionally substituted by nitro or $C_1$-$C_5$-alkoxy, or represents $C_6$-$C_{10}$-arylthio which is optionally substituted by nitro, amino, $C_1$-$C_6$-alkyl or $C_1$-$C_4$-alkoxy, or represents $C_6$-$C_{12}$-arylamino, $C_1$-$C_7$-alkylamino, di($C_1$-$C_7$-alkyl)amino, $C_3$-$C_6$-cycloalkylamino or a structure of

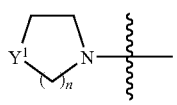

wherein n denotes an integer of 1 or 2 and $Y^1$ represents O, $CH_2$ or N—R (R represents $C_1$-$C_7$-alkyl), and $X^2$, $X^3$ and $X^4$ independently of one another represent hydrogen, amino, hydroxy, halogen, $C_1$-$C_7$-alkyl, $C_1$-$C_5$-alkoxy, or $C_1$-$C_7$-alkylamino.

Most preferred compounds are those wherein ----- represents single bond, $R^1$, $R^3$, $R^7$ and $R^8$ independently of one another represent hydrogen, $R^2$ represents hydrogen or methyl, $R^4$ and $R^5$ independently of one another represent t-butylcarbonyloxymethyl, isopropoxycarbonyloxymethyl or 2,2,2-trifluoroethyl, Y represents —O—, Q represents

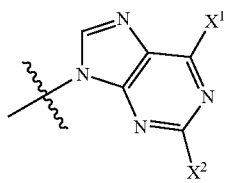

wherein $X^1$ represents hydrogen, hydroxy, ethoxy, 4-methoxyphenylthio or 4-nitrophenylthio, and $X^2$ represents amino.

Typical examples of the compound of formula (1) according to the present invention are described in the following Tables 1 and 7.

TABLE 1

| COM. NO. | STRUCTURE |
|---|---|
| 1 | |
| 2 | 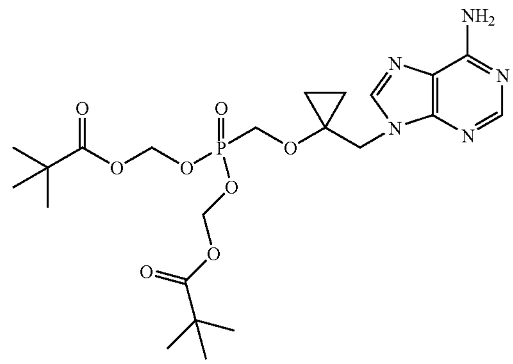 |
| 3 | 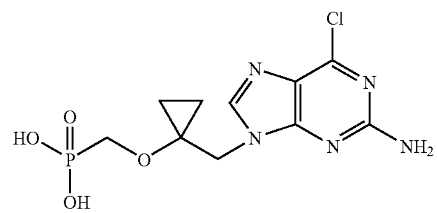 |
| 4 | 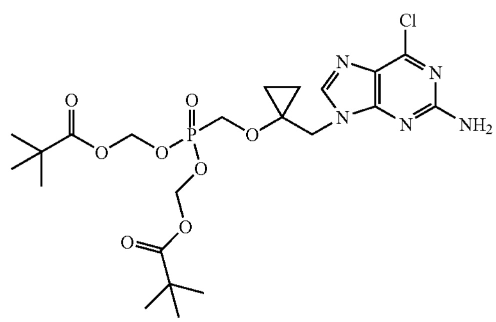 |
| 5 | 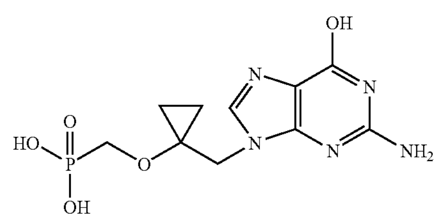 |
| 6 | 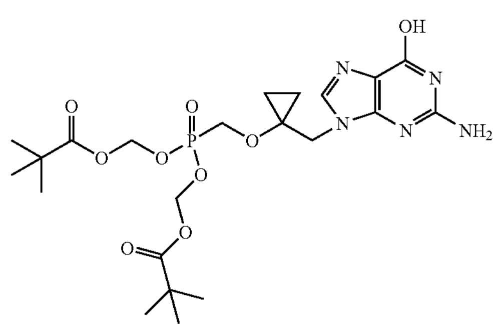 |

TABLE 1-continued
| COM. NO. | STRUCTURE |
|---|---|
| 7 | 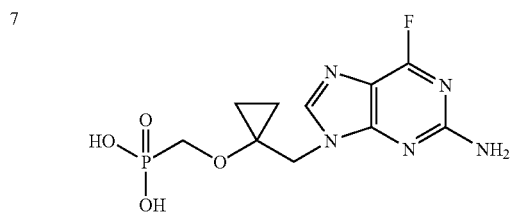 |
| 8 | 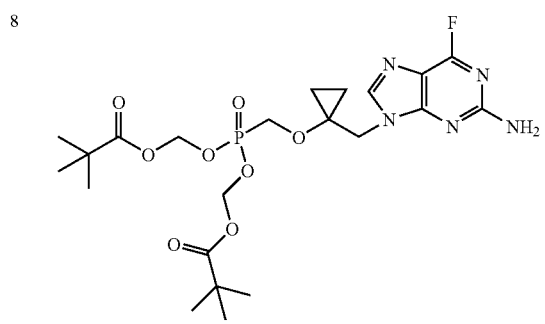 |
| 9 | 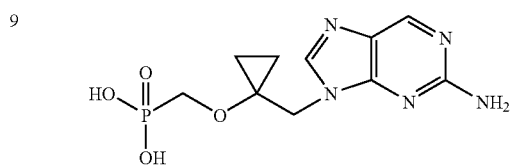 |
| 10 | 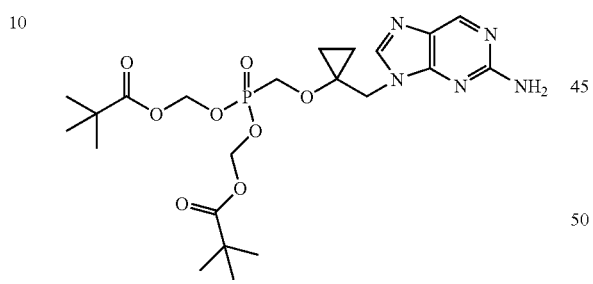 |
| 11 | 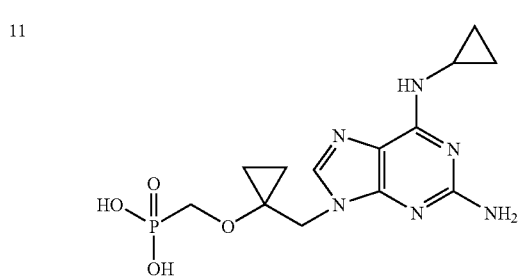 |
TABLE 1-continued
| COM. NO. | STRUCTURE |
|---|---|
| 12 | 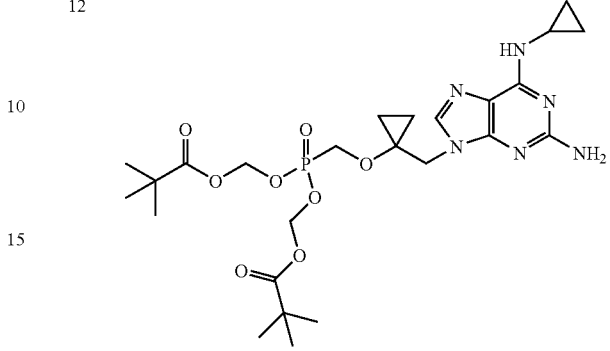 |
| 13 | 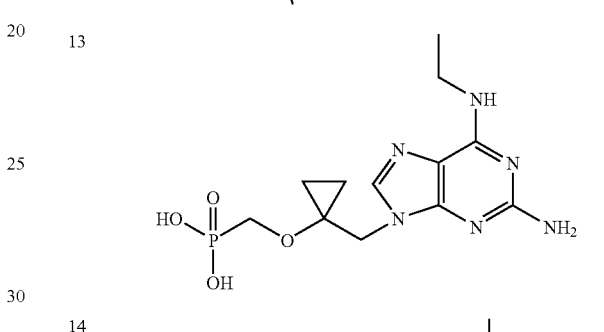 |
| 14 | 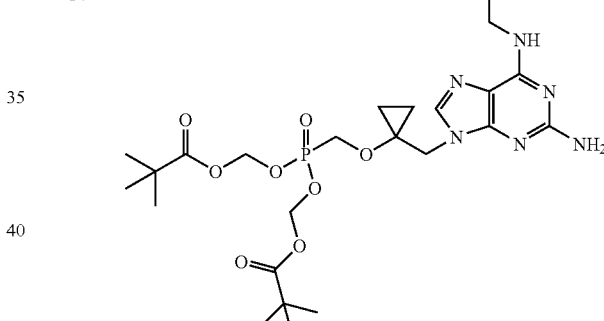 |
| 15 | 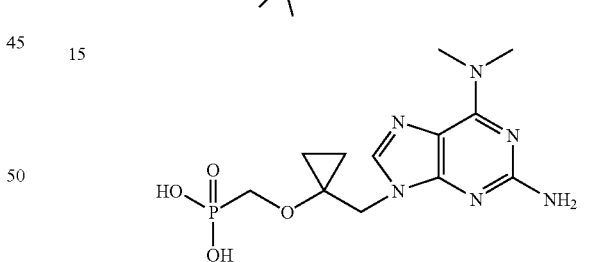 |
| 16 | 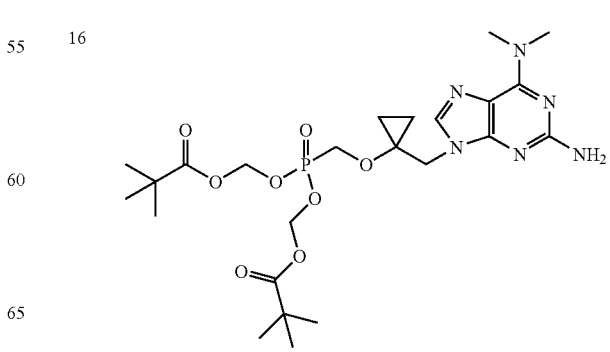 |

TABLE 1-continued

| COM. NO. | STRUCTURE |
|---|---|
| 17 | [structure: phosphonic acid-CH2-O-C(cyclopropyl)-CH2-N(purine with 6-NHiPr, 2-NH2)] |
| 18 | [structure: bis(pivaloyloxymethyl) phosphonate-CH2-O-C(cyclopropyl)-CH2-N(purine with 6-NHiPr, 2-NH2)] |
| 19 | [structure: phosphonic acid-CH2-O-C(cyclopropyl)-CH2-N(purine with 6-NH2, 2-NH2)] |
| 20 | [structure: bis(pivaloyloxymethyl) phosphonate-CH2-O-C(cyclopropyl)-CH2-N(purine with 6-NH2, 2-NH2)] |
| 21 | [structure: phosphonic acid-CH2-O-C(cyclopropyl)-CH2-N(purine with 6-OMe, 2-NH2)] |

TABLE 1-continued

| COM. NO. | STRUCTURE |
|---|---|
| 22 | [structure: bis(pivaloyloxymethyl) phosphonate-CH2-O-C(cyclopropyl)-CH2-N(purine with 6-OMe, 2-NH2)] |
| 23 | [structure: phosphonic acid-CH2-O-C(cyclopropyl)-CH2-N(purine with 6-OEt, 2-NH2)] |
| 24 | [structure: bis(pivaloyloxymethyl) phosphonate-CH2-O-C(cyclopropyl)-CH2-N(purine with 6-OEt, 2-NH2)] |
| 25 | [structure: phosphonic acid-CH2-O-C(cyclopropyl)-CH2-N(purine with 6-CH3, 2-NH2)] |
| 26 | [structure: bis(pivaloyloxymethyl) phosphonate-CH2-O-C(cyclopropyl)-CH2-N(purine with 6-CH3, 2-NH2)] |

TABLE 1-continued
| COM. NO. | STRUCTURE |
|---|---|
| 27 | 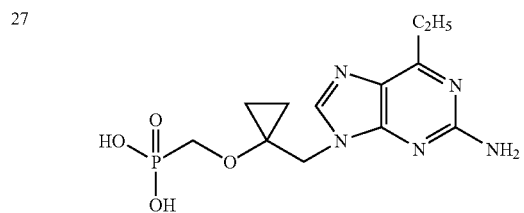 |
| 28 | 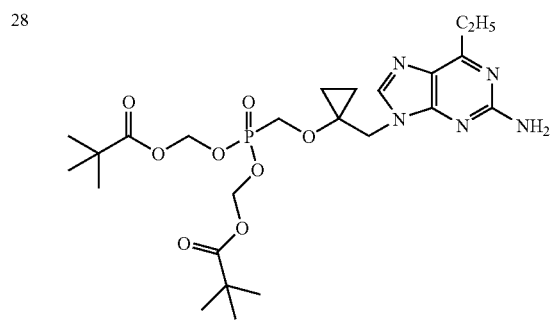 |
| 29 | 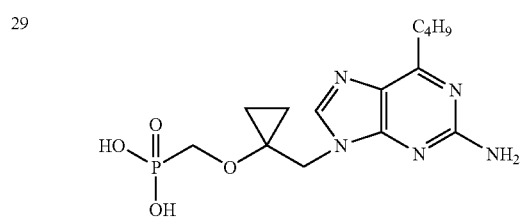 |
| 30 | 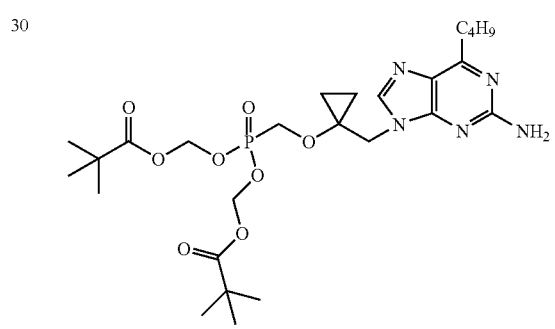 |
| 31 | 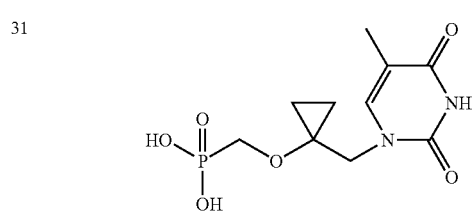 |
TABLE 1-continued
| COM. NO. | STRUCTURE |
|---|---|
| 32 | 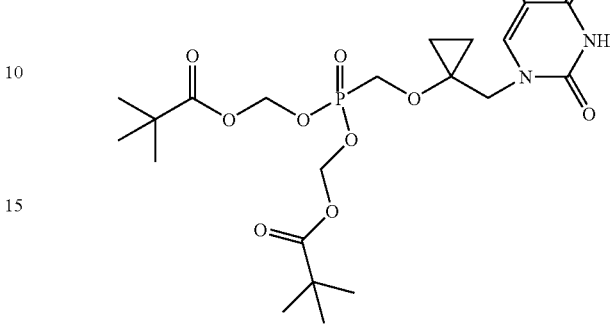 |
| 33 | 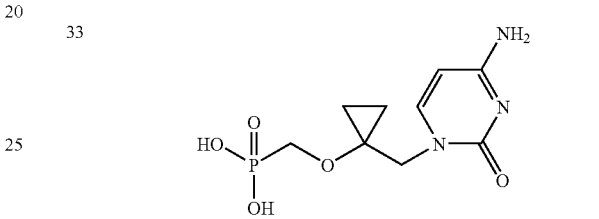 |
| 34 | 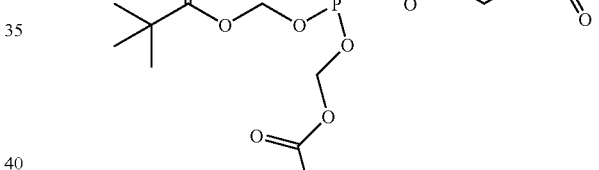 |
| 35 | 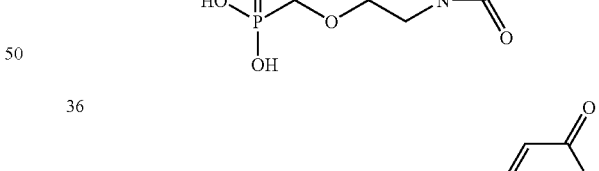 |
| 36 | 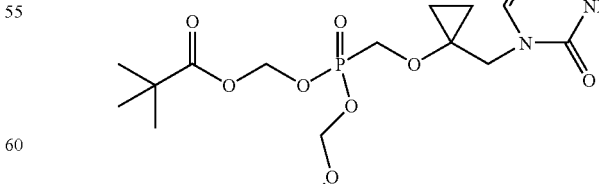 |

TABLE 1-continued

| COM. NO. | STRUCTURE |
|---|---|
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 2

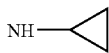

| COM. NO. | X¹ | X² | R⁴ | R⁵ |
|---|---|---|---|---|
| 45 | OH | $NH_2$ | $CH_2CF_3$ | $CH_2CF_3$ |
| 46 | Cl | $NH_2$ | $CH_2CF_3$ | $CH_2CF_3$ |
| 47 | $NH_2$ | $NH_2$ | $CH_2CF_3$ | $CH_2CF_3$ |
| 48 | $NH_2$ | H | $CH_2CF_3$ | $CH_2CF_3$ |
| 49 | H | $NH_2$ | $CH_2CF_3$ | $CH_2CF_3$ |
| 50 | 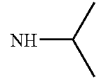 | $NH_2$ | $CH_2CF_3$ | $CH_2CF_3$ |
| 51 | $NHC_2H_5$ | $NH_2$ | $CH_2CF_3$ | $CH_2CF_3$ |
| 52 | $N(CH_3)_2$ | $NH_2$ | $CH_2CF_3$ | $CH_2CF_3$ |
| 53 | 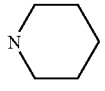 | $NH_2$ | $CH_2CF_3$ | $CH_2CF_3$ |
| 54 | $OCH_3$ | $NH_2$ | $CH_2CF_3$ | $CH_2CF_3$ |
| 55 | $CH_3$ | $NH_2$ | $CH_2CF_3$ | $CH_2CF_3$ |
| 56 | $C_2H_5$ | $NH_2$ | $CH_2CF_3$ | $CH_2CF_3$ |
| 57 | 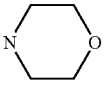 | $NH_2$ | $CH_2CF_3$ | $CH_2CF_3$ |
| 58 | 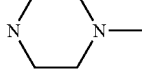 | $NH_2$ | $CH_2CF_3$ | $CH_2CF_3$ |
| 59 | 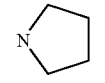 | $NH_2$ | $CH_2CF_3$ | $CH_2CF_3$ |
| 60 | 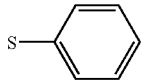 | $NH_2$ | $CH_2CF_3$ | $CH_2CF_3$ |
| 61 | 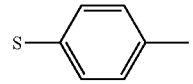 | $NH_2$ | $CH_2CF_3$ | $CH_2CF_3$ |
| 62 |  | $NH_2$ | $CH_2CF_3$ | $CH_2CF_3$ |
| 63 |  | $NH_2$ | $CH_2CF_3$ | $CH_2CF_3$ |
| 64 | 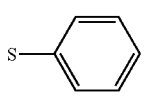 | $NH_2$ | $CH_2CF_3$ | $CH_2CF_3$ |
| 65 | 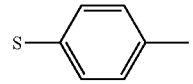 | $NH_2$ | H | H |

TABLE 2-continued
| COM. NO. | X¹ | X² | R⁴ | R⁵ |
|---|---|---|---|---|
| 66 | 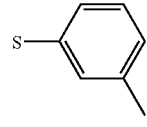 | NH$_2$ | H | H |
| 67 | 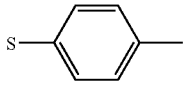 | NH$_2$ | H | H |
| 68 | 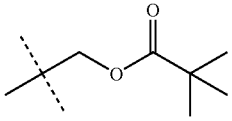 | NH$_2$ | 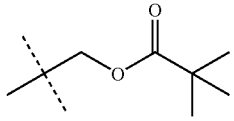 | 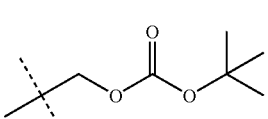 |
| 69 | H | NH$_2$ | 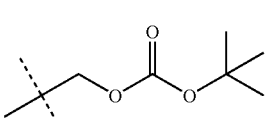 | 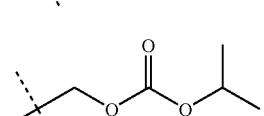 |
| 70 | H | NH$_2$ | 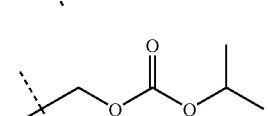 | 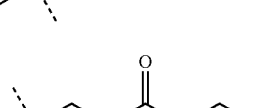 |
| 71 | H | NH$_2$ | 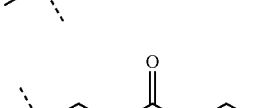 | 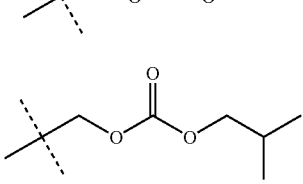 |
| 72 | H | NH$_2$ | 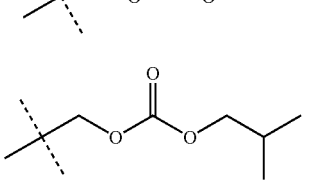 | 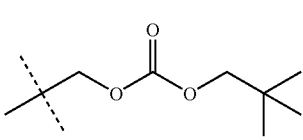 |
| 73 | H | NH$_2$ | 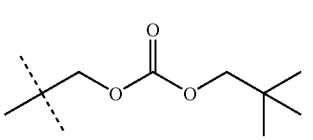 | 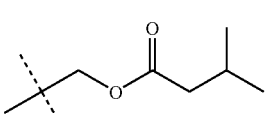 |
| 74 | H | NH$_2$ | 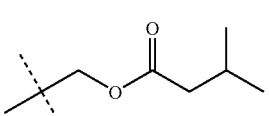 | 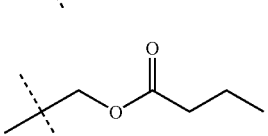 |
| 75 | H | NH$_2$ | 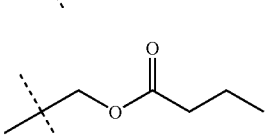 | |

TABLE 2-continued

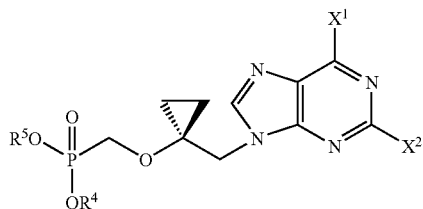

| COM. NO. | X¹ | X² | R⁴ | R⁵ |
|---|---|---|---|---|
| 76 | H | NH₂ | cyclopentanecarboxyloxymethyl | cyclopentanecarboxyloxymethyl |
| 77 | H | NH₂ | (3,3-dimethylbutanoyloxy)methyl | (3,3-dimethylbutanoyloxy)methyl |
| 78 | H | NH₂ | (isobutyryloxy)methyl | (isobutyryloxy)methyl |
| 79 | S-C₆H₄-OMe (4-methoxyphenylthio) | NH₂ | (pivaloyloxy)methyl | (pivaloyloxy)methyl |
| 80 | H | NH₂ | (pyrrolidine-1-carbonyloxy)methyl | (pyrrolidine-1-carbonyloxy)methyl |
| 81 | H | NH₂ | (piperidine-1-carbonyloxy)methyl | (piperidine-1-carbonyloxy)methyl |
| 82 | H | NH₂ | (morpholine-4-carbonyloxy)methyl | (morpholine-4-carbonyloxy)methyl |
| 83 | OH | NH₂ | (tert-butoxycarbonyloxy)methyl | (tert-butoxycarbonyloxy)methyl |
| 84 | OH | NH₂ | (isopropoxycarbonyloxy)methyl | (isopropoxycarbonyloxy)methyl |

TABLE 2-continued

Structure: R⁵O-P(=O)(OR⁴)-CH₂-O-C(cyclopropyl)-CH₂-N(purine with X¹ at 6-position, X² at 2-position)

| COM. NO. | X¹ | X² | R⁴ | R⁵ |
|---|---|---|---|---|
| 85 | S-C₆H₄-OMe (4-) | NH₂ | -CH₂C(CH₃)₂-O-C(=O)-O-CH(CH₃)₂ | -CH₂C(CH₃)₂-O-C(=O)-O-CH(CH₃)₂ |
| 86 | OH | NH₂ | -CH₂C(CH₃)₂-O-C(=O)-cyclopentyl | -CH₂C(CH₃)₂-O-C(=O)-cyclopentyl |
| 87 | S-C₆H₄-NO₂ (4-) | NH₂ | -CH₂C(CH₃)₂-O-C(=O)-C(CH₃)₃ | -CH₂C(CH₃)₂-O-C(=O)-C(CH₃)₃ |
| 88 | S-C₆H₄-NO₂ (4-) | NH₂ | -CH₂C(CH₃)₂-O-C(=O)-O-CH(CH₃)₂ | -CH₂C(CH₃)₂-O-C(=O)-O-CH(CH₃)₂ |
| 89 | NH₂ | H | -CH₂C(CH₃)₂-O-C(=O)-O-CH(CH₃)₂ | -CH₂C(CH₃)₂-O-C(=O)-O-CH(CH₃)₂ |
| 90 | NH₂ | H | -CH₂C(CH₃)₂-O-C(=O)-CH₂-CH(CH₃)₂ | -CH₂C(CH₃)₂-O-C(=O)-CH₂-CH(CH₃)₂ |
| 91 | NH₂ | H | -CH₂C(CH₃)₂-O-C(=O)-cyclopentyl | -CH₂C(CH₃)₂-O-C(=O)-cyclopentyl |
| 92 | S-C₆H₄-OMe (4-) | NH₂ | -CH₂C(CH₃)₂-O-C(=O)-O-C(CH₃)₃ | -CH₂C(CH₃)₂-O-C(=O)-O-C(CH₃)₃ |
| 93 | S-C₆H₄-NO₂ (4-) | NH₂ | -CH₂C(CH₃)₂-O-C(=O)-O-C(CH₃)₃ | -CH₂C(CH₃)₂-O-C(=O)-O-C(CH₃)₃ |
| 94 | NH₂ | H | H | H |
| 95 | S-C₆H₄-NO₂ (4-) | NH₂ | H | H |

TABLE 2-continued

| COM. NO. | X¹ | X² | R⁴ | R⁵ |
|---|---|---|---|---|
| 96 | S-C₆H₄-OMe | NH$_2$ | H | H |

TABLE 3

| COM. NO. | X¹ | X² | R⁴ | R⁵ |
|---|---|---|---|---|
| 97 | OH | NH$_2$ | H | H |
| 98 | H | NH$_2$ | H | H |
| 99 | S-C₆H₄-OMe | NH$_2$ | H | H |
| 100 | S-C₆H₄-NO$_2$ | NH$_2$ | H | H |
| 101 | S-C₆H₄-CH$_3$ | NH$_2$ | H | H |
| 102 | NH$_2$ | NH$_2$ | H | H |
| 103 | NH$_2$ | H | H | H |
| 104 | OH | H | H | H |
| 105 | OH | NH$_2$ | -CH$_2$-O-C(O)-C(CH$_3$)$_3$ | -CH$_2$-O-C(O)-C(CH$_3$)$_3$ |
| 106 | H | NH$_2$ | -CH$_2$-O-C(O)-C(CH$_3$)$_3$ | -CH$_2$-O-C(O)-C(CH$_3$)$_3$ |
| 107 | NH$_2$ | H | -CH$_2$-O-C(O)-C(CH$_3$)$_3$ | -CH$_2$-O-C(O)-C(CH$_3$)$_3$ |

TABLE 3-continued

| COM. NO. | X¹ | X² | R⁴ | R⁵ |
|---|---|---|---|---|
| 108 | S-C₆H₄-OMe | NH₂ | CH₂-O-C(=O)-C(CH₃)₃ | CH₂-O-C(=O)-C(CH₃)₃ |
| 109 | OH | NH₂ | CH₂-O-C(=O)-O-CH(CH₃)₂ | CH₂-O-C(=O)-O-CH(CH₃)₂ |
| 110 | H | NH₂ | CH₂-O-C(=O)-O-CH(CH₃)₂ | CH₂-O-C(=O)-O-CH(CH₃)₂ |
| 111 | NH₂ | H | CH₂-O-C(=O)-O-CH(CH₃)₂ | CH₂-O-C(=O)-O-CH(CH₃)₂ |
| 112 | S-C₆H₄-OMe | NH₂ | CH₂-O-C(=O)-O-CH(CH₃)₂ | CH₂-O-C(=O)-O-CH(CH₃)₂ |
| 113 | S-C₆H₄-OMe | NH₂ | CH₂-O-C(=O)-O-C(CH₃)₃ | CH₂-O-C(=O)-O-C(CH₃)₃ |
| 114 | S-C₆H₄-OMe | NH₂ | CH₂CF₃ | CH₂CF₃ |
| 115 | S-C₆H₄-NO₂ | NH₂ | CH₂CF₃ | CH₂CF₃ |
| 116 | S-C₆H₄-NO₂ | NH₂ | CH₂-O-C(=O)-O-C(CH₃)₃ | CH₂-O-C(=O)-O-C(CH₃)₃ |
| 117 | S-C₆H₄-NO₂ | NH₂ | CH₂-O-C(=O)-O-CH(CH₃)₂ | CH₂-O-C(=O)-O-CH(CH₃)₂ |

TABLE 3-continued
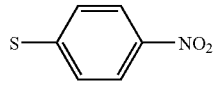
| COM. NO. | X¹ | X² | R⁴ | R⁵ |
|---|---|---|---|---|
| 118 | 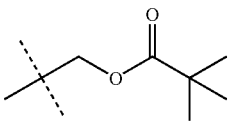 | NH₂ | 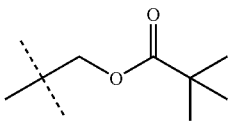 | 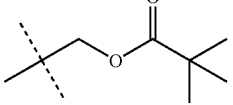 |
TABLE 4
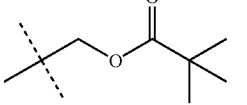
| COM. NO. | Z | X¹ | X² | R⁴ | R⁵ |
|---|---|---|---|---|---|
| 119 | H | OH | NH₂ | H | H |
| 120 | H | H | NH₂ | H | H |
| 121 | H | NH₂ | H | H | H |
| 122 | CH₃ | OH | NH₂ | H | H |
| 123 | CH₃ | H | NH₂ | H | H |
| 124 | CH₃ | NH₂ | H | H | H |
| 125 | C₂H₅ | NH₂ | H | H | H |
| 126 | CH₃ | NH₂ | H | 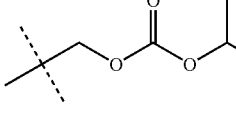 | 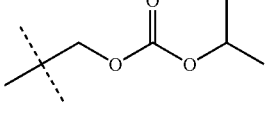 |
| 127 | CH₃ | NH₂ | H | 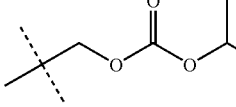 | 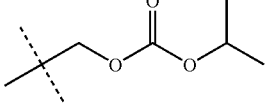 |
| 128 | C₂H₅ | H | NH₂ | 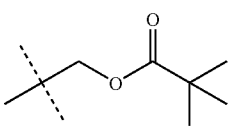 | 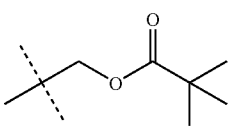 |
| 129 | C₂H₅ | H | NH₂ | 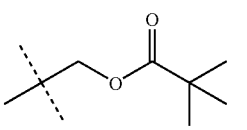 | 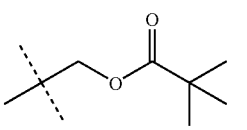 |

TABLE 5

| COM. NO. | Z | X¹ | X² | R⁴ | R⁵ |
| --- | --- | --- | --- | --- | --- |
| 130 | H | OH | $NH_2$ | H | H |
| 131 | H | H | $NH_2$ | H | H |
| 132 | H | $NH_2$ | H | H | H |
| 133 | H | OH | $NH_2$ | -CH₂-O-C(O)-C(CH₃)₃ | -CH₂-O-C(O)-C(CH₃)₃ |
| 134 | H | $NH_2$ | H | -CH₂-O-C(O)-C(CH₃)₃ | -CH₂-O-C(O)-C(CH₃)₃ |
| 135 | $CH_3$ | OH | $NH_2$ | H | H |
| 136 | $CH_3$ | H | $NH_2$ | H | H |
| 137 | $CH_3$ | $NH_2$ | H | H | H |

TABLE 6

| COM. NO. | Z | X¹ | X² | R⁴ | R⁵ |
| --- | --- | --- | --- | --- | --- |
| 138 | H | OH | $NH_2$ | H | H |
| 139 | H | H | $NH_2$ | H | H |
| 140 | H | $NH_2$ | H | H | H |
| 141 | -S-C₆H₄-CH₃ | | $NH_2$ | H | H |
| 142 | $CH_3$ | OH | $NH_2$ | H | H |
| 143 | $CH_3$ | $NH_2$ | H | H | H |
| 144 | $CH_3$ | H | $NH_2$ | H | H |
| 145 | $CH_3$ | $NH_2$ | H | -CH₂-O-C(O)-C(CH₃)₃ | -CH₂-O-C(O)-C(CH₃)₃ |

TABLE 7

[Structure: R⁵O-P(=O)(OR⁴)-CH₂-O-C(cyclopropyl with gem-dimethyl)(CH₂-purine with X¹ at 6-position, X² at 2-position)]

| COM. NO. | X¹ | X² | R⁴ | R⁵ |
|---|---|---|---|---|
| 146 | OH | NH₂ | H | H |
| 147 | H | NH₂ | H | H |
| 148 | NH₂ | H | H | H |
| 149 | OH | NH₂ | -CH₂-O-C(=O)-C(CH₃)₃ | -CH₂-O-C(=O)-C(CH₃)₃ |
| 150 | H | NH₂ | -CH₂-O-C(=O)-C(CH₃)₃ | -CH₂-O-C(=O)-C(CH₃)₃ |
| 151 | NH₂ | H | -CH₂-O-C(=O)-C(CH₃)₃ | -CH₂-O-C(=O)-C(CH₃)₃ |
| 152 | NH₂ | H | -CH₂-O-C(=O)-O-CH(CH₃)₂ | -CH₂-O-C(=O)-O-CH(CH₃)₂ |
| 153 | OH | NH₂ | -CH₂-O-C(=O)-O-CH(CH₃)₂ | -CH₂-O-C(=O)-O-CH(CH₃)₂ |

More particularly preferable compounds among the compounds described in the above Tables 1 and 7 are as follows:

({1-[(6-amino-9H-purin-9-yl)methyl]cyclopropyl}oxy)methylphosphonic acid (Compound 1);

3-[({1-[(6-amino-9H-purin-9-yl)methyl]cyclopropyl}oxy)methyl]-8,8-dimethyl-3,7-dioxo-2,4,6-trioxa-3$^5$-phosphanon-1-yl pivalate (Compound 2);

({1-[(2-amino-6-chloro-9H-purin-9-yl)methyl]cyclopropyl}oxy)methylphosphonic acid (Compound 3);

3-[({1-[(2-amino-6-chloro-9H-purin-9-yl)methyl]cyclopropyl}oxy)methyl]-8,8-dimethyl-3,7-dioxo-2,4,6-trioxa-3$^5$-phosphanon-1-yl pivalate (Compound 4);

({1-[(2-amino-6-hydroxy-9H-purin-9-yl)methyl]cyclopropyl}oxy)methylphosphonic acid (Compound 5);

3-[({1-[(2-amino-6-hydroxy-9H-purin-9-yl)methyl]cyclopropyl}oxy)methyl]-8,8-dimethyl-3,7-dioxo-2,4,6-trioxa-3$^5$-phosphanon-1-yl pivalate (Compound 6);

({1-[(2-amino-6-fluoro-9H-purin-9-yl)methyl]cyclopropyl}oxy)methylphosphonic acid (Compound 7);

3-[({1-[(2-amino-6-fluoro-9H-purin-9-yl)methyl]cyclopropyl}oxy)methyl]-8,8-dimethyl-3,7-dioxo-2,4,6-trioxa-3$^5$-phosphanon-1-yl pivalate (Compound 8);

({1-[(2-amino-9H-purin-9-yl)methyl]cyclopropyl}oxy)methylphosphonic acid (Compound 9);

3-[({1-[(2-amino-9H-purin-9-yl)methyl]cyclopropyl}oxy)methyl]-8,8-dimethyl-3,7-dioxo-2,4,6-trioxa-3$^5$-phosphanon-1-yl pivalate (Compound 10);

({1[(2-amino-6-cyclopropylamino-9H-purin-9-yl)methyl]cyclopropyl}oxy)meth-ylphosphonic acid (Compound 11);

3-[({1-[(2-amino-6-cyclopropylamino-9H-purin-9-yl)methyl]cyclopropyl}oxy)methyl]-8,8-dimethyl-3,7-dioxo-2,4,6-trioxa-3$^5$-phosphanon-1-yl pivalate (Compound 12);

[(1-{[2-amino-6-(dimethylamino)-9H-purin-9-yl]methyl}cyclopropyl)oxy]methylphosphonic acid (Compound 15);

3-{[(1-{[2-amino-6-(dimethylamino)-9H-purin-9-yl]methyl}cyclopropyl)oxy]methyl}-8,8-dimethyl-3,7-dioxo-2,4,6-trioxa-3$^5$-phosphanon-1-yl pivalate (Compound 16);

[(1-{[2-amino-6-(isopropylamino)-9H-purin-9-yl]methyl}cyclopropyl)oxy]methylphosphonic acid (Compound 17);

3-{[(1-{[2-amino-6-(isopropylamino)-9H-purin-9-yl]
methyl}cyclopropyl)oxy]methyl}-8,8-dimethyl-3,7-di-
oxo-2,4,6-trioxa-3$8^5$-phosphanon-1-yl pivalate (Compound 18);

({1-[(2,6-diamino-9H-purin-9-yl)methyl]cyclopropyl}oxy)
methylphosphonic acid (Compound 19);

3-[({1-[(2,6-diamino-9H-purin-9-yl)methyl]
cyclopropyl}oxy)methyl]-8,8-dimethyl-3,7-dioxo-2,4,6-
trioxa-3$8^5$-phosphanon-1-yl pivalate (Compound 20);

({1-[(2-amino-6-methoxy-9H-purin-9-yl)methyl]
cyclopropyl}oxy)methylphosphonic acid (Compound 21);

3-[({1-[(2-amino-6-methoxy-9H-purin-9-yl)methyl]
cyclopropyl}oxy)methyl]-8,8-dimethyl-3,7-dioxo-2,4,6-
trioxa-3$8^5$-phosphanon-1-yl pivalate (Compound 22);

({1-[(2-amino-6-ethoxy-9H-purin-9-yl)methyl]
cyclopropyl}oxy)methylphosphonic acid (Compound 23);

3-[({1-[(2-amino-6-ethoxy-9H-purin-9-yl)methyl]
cyclopropyl}oxy)methyl]-8,8-dimethyl-3,7-dioxo-2,4,6-
trioxa-3$8^5$-phosphanon-1-yl pivalate (Compound 24);

({1-[(2-amino-6-methyl-9H-purin-9-yl)methyl]
cyclopropyl}oxy)methylphosphonic acid (Compound 25);

3-[({1-[(2-amino-6-methyl-9H-purin-9-yl)methyl]
cyclopropyl}oxy)methyl]-8,8-dimethyl-3,7-dioxo-2,4,6-
trioxa-3$8^5$-phosphanon-1-yl pivalate (Compound 26);

[(1-{[5-methyl-2,4-dioxo-3,4-dihydro-1(2H)-pyrimidinyl]
methyl}cyclopropyl)oxy]methylphosphonic acid (Compound 31);

8,8-dimethyl-3-{[(1-{[5-methyl-2,4-dioxo-3,4-dihydro-1
(2H)-pyrimidinyl]methyl}cyclopropyl)oxy]methyl}-3,7-
dioxo-2,4,6-trioxa-3$8^5$-phosphanon-1-yl pivalate (Compound 32);

[(1-{[2-amino-6-(4-morpholinyl)-9H-purin-9-yl]
methyl}cyclopropyl)oxy]methylphosphonic acid (Compound 37);

3-{[(1-{[2-amino-6-(4-morpholinyl)-9H-purin-9-yl]
methyl}cyclopropyl)oxy]met-hyl}-8,8-dimethyl-3,7-di-
oxo-2,4,6-trioxa-3$8^5$-phosphanon-1-yl pivalate (Compound 38);

bis(2,2,2-trifluoroethyl)({1-[(2-amino-6-hydroxy-9H-purin-
9-yl)methyl]cyclopropyl}oxy)methylphosphonate (Compound 45);

bis(2,2,2-trifluoroethyl)({1-[(2-amino-6-chloro-9H-purin-
9-yl)methyl]cyclopropyl}oxy)methylphosphonate (Compound 46);

bis(2,2,2-trifluoroethyl)({1-[(2,6-diamino-9H-purin-9-yl)
methyl]cyclopropyl}oxy)methylphosphonate (Compound 47);

bis(2,2,2-trifluoroethyl)({1-[(6-amino-9H-purin-9-yl)methyl]cyclopropyl}oxy)methylphosphonate (Compound 48);

bis(2,2,2-trifluoroethyl)({1-[(2-amino-9H-purin-9-yl)methyl]cyclopropyl}oxy)methylphosphonate (Compound 49);

bis(2,2,2-trifluoroethyl)({1-[(2-amino-6-dimethylamino-
9H-purin-9-yl)methyl]cyclopropyl}oxy)methylphosphonate (Compound 52);

bis(2,2,2-trifluoroethyl)({1-[(2-amino-6-isopropylamino-
9H-purin-9-yl)methyl]cyclopropyl}oxy)methylphosphonate (Compound 53);

bis(2,2,2-trifluoroethyl)({1-[(2-amino-6-methoxy-9H-purin-9-yl)methyl]cyclopropyl}oxy)methylphosphonate (Compound 54);

bis(2,2,2-trifluoroethyl)[(1-{[2-amino-6-(4-morpholinyl)-
9H-purin-9-yl]methyl}cyclopropyl)oxy]methylphosphonate (Compound 58);

bis(2,2,2-trifluoroethyl)[(1-{[2-amino-6-(phenylsulfanyl)-
9H-purin-9-yl]methyl}cyclopropyl)oxy]methylphosphonate (Compound 61);

bis(2,2,2-trifluoroethyl){[1-({2-amino-6-[(4-methylphenyl)
sulfanyl]-9H-purin-9-yl}methyl)cyclopropyl]
oxy}methylphosphonate (Compound 62);

bis(2,2,2-trifluoroethyl){[1-({2-amino-6-[(4-methoxyphenyl)sulfanyl]-9H-purin-9-yl}methyl)cyclopropyl]
oxy}methylphosphonate (Compound 63);

bis(2,2,2-trifluoroethyl){[1-({2-amino-6-[(4-nitrophenyl)
sulfanyl]-9H-purin-9-yl}methyl)cyclopropyl]
oxy}methylphosphonate (Compound 64);

[(1-{[2-amino-6-(phenylsulfanyl)-9H-purin-9-yl]
methyl}cyclopropyl)oxy]methylphosphonic acid (Compound 65);

{[1-({2-amino-6-[(4-methylphenyl)sulfanyl]-9H-purin-9-
yl}methyl)cyclopropyl]oxy}methylphosphonic acid (Compound 66);

3-({[1-({2-amino-6-[(4-methylphenyl)sulfanyl]-9H-purin-
9-yl}methyl)cyclopropyl]oxy}methyl)-8,8-dimethyl-3,7-
dioxo-2,4,6-trioxa-3$8^5$-phosphanon-1-yl pivalate (Compound 68);

bis{[(t-butoxycarbonyl)oxy]methyl}({1-[(2-amino-9H-purin-9-yl)methyl]cyclopropyl}oxy)methylphosphonate (Compound 69);

bis{[(isopropoxycarbonyl)oxy]methyl}({1-[(2-amino-9H-purin-9-yl)methyl]cyclopropyl}oxy)methylphosphonate (Compound 70);

bis{[(ethoxycarbonyl)oxy]methyl}({1-[(2-amino-9H-purin-9-yl)methyl]cyclopropyl}oxy)methylphosphonate (Compound 71);

bis{[(isobutoxycarbonyl)oxy]methyl}({1-[(2-amino-9H-purin-9-yl)methyl]cyclopropyl}oxy)methylphosphonate (Compound 72);

3-[({1-[(2-amino-9H-purin-9-yl)methyl]cyclopropyl}oxy)
methyl]-9-methyl-3,7-dioxo-2,4,6-trioxa-3$8^5$-phosphadec-1-yl 3-methylbutanoate (Compound 74);

3-[({1-[(2-amino-9H-purin-9-yl)methyl]cyclopropyl}oxy)
methyl]-8-methyl-3,7-dioxo-2,4,6-trioxa-3$8^5$-phosphanon-1-yl 2-methylpropanoate (Compound 78);

3-({[1-({2-amino-6-[(4-methoxyphenyl)sulfanyl]-9H-purin-9-yl}methyl)cyclo propyl]oxy}methyl)-8,8-dimethyl-
3,7-dioxo-2,4,6-trioxa-3$8^5$-phosphanon-1-yl pivalate (Compound 79);

3-[({1-[(2-amino-9H-purin-9-yl)methyl]cyclopropyl}oxy)
methyl]-3,7-dioxo-7-(1-pyrrolidinyl)-2,4,6-trioxa-3$8^5$-
phosphahept-1-yl 1-pyrrolidinecarboxylate (Compound 80);

3-[({1-[(2-amino-9H-purin-9-yl)methyl]cyclopropyl}oxy)
methyl]-3,7-dioxo-7-(1-piperidinyl)-2,4,6-trioxa-3$8^5$-
phosphahept-1-yl 1-piperidinecarboxylate (Compound 81);

3-[({1-[(2-amino-9H-purin-9-yl)methyl]cyclopropyl}oxy)
methyl]-7-(4-morpholinyl)-3,7-dioxo-2,4,6-trioxa-3$8^5$-
phosphahept-1-yl 4-morpholinecarboxylate (Compound 82);

bis{[(t-butoxycarbonyl)oxy]methyl}[(1-{[2-amino-6-hydroxy-9H-purin-9-yl]methyl}cyclopropyl)oxy]methylphosphonate (Compound 83);

bis{[(isopropoxycarbonyl)oxy]methyl}[(1-{[2-amino-6-hydroxy-9H-purin-9-yl]methyl}cyclopropyl)oxy]methylphosphonate (Compound 84);

bis{[(isopropoxycarbonyl)oxy]methyl}{[1-({2-amino-[6-
(4-methoxyphenyl)sulfanyl]-9H-purin-9-yl}methyl)cyclopropyl]oxy}methylphosphonate (Compound 85);

3-[({1-[(2-amino-6-hydroxy-9H-purin-9-yl)methyl] cyclopropyl}oxy)methyl]-7-cyclopentyl-3,7-dioxo-2,4,6-trioxa-3$8^5$-phosphahept-1-yl cyclopentanecarboxylate (Compound 86);

3-({[1-({2-amino-[6-(4-nitrophenyl)sulfanyl]-9H-purin-9-yl}methyl)cyclopropyl]oxy}methyl)-8,8-dimethyl-3,7-dioxo-2,4,6-trioxa-3$8^5$-phosphanon-1-yl pivalate (Compound 87);

bis{[(isopropoxycarbonyl)oxy]methyl}{[1-({2-amino-[6-(4-nitrophenyl)sulfanyl]-9H-purin-9-yl}methyl)cyclopropyl]oxy}methylphosphonate (Compound 88);

bis{[(isopropoxycarbonyl)oxy]methyl}({1-[(6-amino-9H-purin-9-yl)methyl]cyclopropyl}oxy)methylphosphonate (Compound 89);

3-[({1-[(6-amino-9H-purin-9-yl)methyl]cyclopropyl}oxy) methyl]-9-methyl-3,7-dioxo-2,4,6-trioxa-3$8^5$-phosphadec-1-yl 3-methylbutanoate (Compound 90);

3-[({1-[(6-amino-9H-purin-9-yl)methyl]cyclopropyl}oxy) methyl]-7-cyclopentyl-3,7-dioxo-2,4,6-trioxa-3$8^5$-phosphahept-1-yl cyclopentanecarboxylate (Compound 91);

bis{[(t-butoxycarbonyl)oxy]methyl}{[1-({2-amino-[6-(4-methoxyphenyl)sulfanyl]-9H-purin-9-yl}methyl)cyclopropyl]oxy}methylphosphonate (Compound 92);

bis{[(t-butoxycarbonyl)oxy]methyl}{[1-({2-amino-[6-(4-nitrophenyl)sulfanyl]-9H-purin-9-yl}methyl)cyclopropyl]oxy}methylphosphonate (Compound 93);

{[1-({2-amino-[6-(4-nitrophenyl)sulfanyl]-9H-purin-9-yl}methyl)cyclopropyl]oxy}methylphosphonic acid (Compound 95);

{[1-({2-amino-[6-(4-methoxyphenyl)sulfanyl]-9H-purin-9-yl}methyl)cyclopropyl]oxy}methylphosphonic acid (Compound 96);

({1-[(2-amino-6-hydroxy-9H-purin-9-yl)methyl]-2-methylcyclopropyl}oxy)methylphosphonic acid (Compound 97);

({1-[(2-amino-9H-purin-9-yl)methyl]-2-methylcyclopropyl}oxy)methylphosphonic acid (Compound 98);

{[1-({2-amino-[6-(4-methoxyphenyl)sulfanyl]-9H-purin-9-yl}methyl)-2-methylcyclopropyl]oxy}methylphosphonic acid (Compound 99);

{[1-({2-amino-[6-(4-nitrophenyl)sulfanyl]-9H-purin-9-yl}methyl)-2-methylcyclopropyl]oxy}methylphosphonic acid (Compound 100);

{[1-({2-amino-[6-(4-methylphenyl)sulfanyl]-9H-purin-9-yl}methyl)-2-methylcyclopropyl]oxy}methylphosphonic acid (Compound 101);

({1-[(2,6-diamino-9H-purin-9-yl)methyl]-2-methylcyclopropyl}oxy)methylphosphonic acid (Compound 102);

({1-[(6-amino-9H-purin-9-yl)methyl]-2-methylcyclopropyl}oxy)methylphosphonic acid (Compound 103);

3-[({1-[(2-amino-6-hydroxy-9H-purin-9-yl)methyl]-2-methylcyclopropyl}oxy)methyl]-8,8-dimethyl-3,7-dioxo-2,4,6-trioxa-3$8^5$-phosphanon-1-yl pivalate (Compound 105);

3-[({1-[(2-amino-9H-purin-9-yl)methyl]-2-methylcyclopropyl}oxy)methyl]-8,8-dimethyl-3,7-dioxo-2,4,6-trioxa-3$8^5$-phosphanon-1-yl pivalate (Compound 106);

3-[({1-[(6-amino-9H-purin-9-yl)methyl]-2-methylcyclopropyl}oxy)methyl]-8,8-dimethyl-3,7-dioxo-2,4,6-trioxa-3$8^5$-phosphanon-1-yl pivalate (Compound 107);

3-({[1-({2-amino-6-[(4-methoxyphenyl)sulfanyl]-9H-purin-9-yl}methyl)-2-methylcyclopropyl]oxy}methyl)-8,8-dimethyl-3,7-dioxo-2,4,6-trioxa-3$8^5$-phosphanon-1-yl pivalate (Compound 108);

bis{[(isopropoxycarbonyl)oxy]methyl}[(1-{[2-amino-6-hydroxy-9H-purin-9-yl]methyl}-2-methylcyclopropyl)oxy] methylphosphonate (Compound 109);

bis{[(isopropoxycarbonyl)oxy]methyl}({1-[(2-amino-9H-purin-9-yl)methyl]-2-methylcyclopropyl}oxy)methylphosphonate (Compound 110);

bis{[(isopropoxycarbonyl)oxy]methyl}{[1-({2-amino-[6-(4-methoxyphenyl)sulfanyl]-9H-purin-9-yl}methyl)-2-methylcyclopropyl]oxy}methylphosphonate (Compound 112);

bis{[(t-butoxycarbonyl)oxy]methyl}{[1-({2-amino-[6-(4-methoxyphenyl)sulfanyl]-9H-purin-9-yl}methyl)-2-methylcyclopropyl]oxy}methylphosphonate (Compound 113);

bis(2,2,2-trifluoroethyl){[1-({2-amino-6-[(4-methoxyphenyl)sulfanyl]-9H-purin-9-yl}methyl)-2-methylcyclopropyl]oxy}methylphosphonate (Compound 114);

bis(2,2,2-trifluoroethyl){[1-({2-amino-6-[(4-nitrophenyl)sulfanyl]-9H-purin-9-yl}methyl)-2-methylcyclopropyl] oxy}methylphosphonate (Compound 115);

bis{[(t-butoxycarbonyl)oxy]methyl}{[1-({2-amino-[6-(4-nitrophenyl)sulfanyl]-9H-purin-9-yl}methyl)-2-methylcyclopropyl]oxy}methylphosphonate (Compound 116);

bis{[(isopropoxycarbonyl)oxy]methyl}{[1-({2-amino-[6-(4-nitrophenyl)sulfanyl]-9H-purin-9-yl}methyl)-2-methylcyclopropyl]oxy}methylphosphonate (Compound 117);

3-({[1-({2-amino-6-[(4-nitrophenyl)sulfanyl]-9H-purin-9-yl}methyl)-2-methylcyclopropyl]oxy}methyl)-8,8-dimethyl-3,7-dioxo-2,4,6-trioxa-3$8^5$-phosphanon-1-yl pivalate (Compound 118);

({1-[(2-amino-6-hydroxy-9H-purin-9-yl)methyl] cyclopropyl}amino)methylphosphonic acid (Compound 119);

({1-[(2-amino-9H-purin-9-yl)methyl]cyclopropyl}amino) methylphosphonic acid (Compound 120);

({1-[(6-amino-9H-purin-9-yl)methyl]cyclopropyl}amino) methylphosphonic acid (Compound 121);

[{1-[(2-amino-6-hydroxy-9H-purin-9-yl)methyl]cyclopropyl}(methyl)amino]methylphosphonic acid (Compound 122);

[{1-[(6-amino-9H-purin-9-yl)methyl]cyclopropyl}(ethyl) amino]methylphosphonic acid (Compound 125);

3-{[{(1-[(6-amino-9H-purin-9-yl)methyl]cyclopropyl}(methyl)amino)methyl]-8,8-dimethyl-3,7-dioxo-2,4,6-trioxa-3$8^5$-phosphanon-1-yl pivalate (Compound 126);

bis{[(isopropoxycarbonyl)oxy]methyl}[{1-[(6-amino-9H-purin-9-yl)methyl]cyclopropyl}(methyl)amino]methylphosphonate (Compound 127);

3-{[{1-[(2-amino-9H-purin-9-yl)methyl]cyclopropyl}(ethyl)amino]methyl}-8,8-dimethyl-3,7-dioxo-2,4,6-trioxa-3$8^5$-phosphanon-1-yl pivalate (Compound 129);

(E)-2-{1-[(2-amino-6-hydroxy-9H-purin-9-yl)methyl] cyclopropyl}ethenylphosphonic acid (Compound 130);

(E)-2-{1-[(2-amino-9H-purin-9-yl)methyl] cyclopropyl}ethenylphosphonic acid (Compound 131);

(E)-2-{1-[(6-amino-9H-purin-9-yl)methyl] cyclopropyl}ethenylphosphonic acid (Compound 132);

3-((E)-2-{1-[(2-amino-6-hydroxy-9H-purin-9-yl)methyl] cyclopropyl}ethenyl)-8,8-dimethyl-3,7-dioxo-2,4,6-trioxa-3$8^5$-phosphanon-1-yl pivalate (Compound 133);

3-((E)-2-{1-[(6-amino-9H-purin-9-yl)methyl] cyclopropyl}ethenyl)-8,8-dimethyl-3,7-dioxo-2,4,6-trioxa-3$8^5$-phosphanon-1-yl pivalate (Compound 134);

(E)-2-{1-[(6-amino-9H-purin-9-yl)methyl]cyclopropyl}-1-propenylphosphonic acid (Compound 137);

2-{1-[(2-amino-6-hydroxy-9H-purin-9-yl)methyl]cyclopropyl}ethylphosphonic acid (Compound 138);

2-{1-[(2-amino-9H-purin-9-yl)methyl]cyclopropyl}ethylphosphonic acid (Compound 139);

2-{1-[(6-amino-9H-purin-9-yl)methyl]cyclopropyl}ethylphosphonic acid (Compound 140);

2-[1-({2-amino-6-[(4-methylphenyl)sulfanyl]-9H-purin-9-yl}methyl)cyclopropyl]ethylphosphonic acid (Compound 141);

2-{1-[(2-amino-6-hydroxy-9H-purin-9-yl)methyl]cyclopropyl}propylphosphonic acid (Compound 142);

2-{1-[(6-amino-9H-purin-9-yl)methyl]cyclopropyl}propylphosphonic acid (Compound 143);

2-{1-[(2-amino-9H-purin-9-yl)methyl]cyclopropyl}propylphosphonic acid (Compound 144);

3-(2-{1-[(6-amino-9H-purin-9-yl)methyl]cyclopropyl}propyl)-8,8-dimethyl-3,7-dioxo-2,4,6-trioxa-3$\lambda^5$-phosphanon-1-yl pivalate (Compound 145);

({1-[(2-amino-6-hydroxy-9H-purin-9-yl)methyl]-2,2-dimethylcyclopropyl}oxy)methylphosphonic acid (Compound 146);

({1-[(2-amino-9H-purin-9-yl)methyl]-2,2-dimethylcyclopropyl}oxy)methylphosphonic acid (Compound 147);

({1-[(6-amino-9H-purin-9-yl)methyl]-2,2-dimethylcyclopropyl}oxy)methylphosphonic acid (Compound 148);

3-[({1-[(2-amino-6-hydroxy-9H-purin-9-yl)methyl]-2,2-dimethylcyclopropyl}oxy)methyl]-8,8-dimethyl-3,7-dioxo-2,4,6-trioxa-3$\lambda^5$-phosphanon-1-yl pivalate (Compound 149);

3-[({1-[(2-amino-9H-purin-9-yl)methyl]-2,2-dimethylcyclopropyl}oxy)methyl]-8,8-dimethyl-3,7-dioxo-2,4,6-trioxa-3$\lambda^5$-phosphanon-1-yl pivalate (Compound 150);

3-[({1-[(6-amino-9H-purin-9-yl)methyl]-2,2-dimethylcyclopropyl}oxy)methyl]-8,8-dimethyl-3,7-dioxo-2,4,6-trioxa-3$\lambda^5$-phosphanon-1-yl pivalate (Compound 151);

bis{[(isopropoxycarbonyl)oxy]methyl}({1-[(6-amino-9H-purin-9-yl)methyl]-2,2-dimethylcyclopropyl}oxy)methylphosphonate (Compound 152); and bis{[(isopropoxycarbonyl)oxy]methyl}[(1-{[2-amino-6-hydroxy-9H-purin-9-yl]methyl}-2,2-dimethylcyclopropyl)oxy]methylphosphonate (Compound 153).

The compound of formula (1) according to the present invention can be prepared by a process as explained below, and thus, it is another object of the present invention to provide such a preparation process. However, conditions of the process, such as for example, reactants, solvents, bases, amounts of the reactants used, etc. are not restricted to those explained below. The compound of the present invention may also be conveniently prepared by optionally combining the various synthetic ways described in the present specification or known in the arts, and such a combination can be easily performed by one of ordinary skill in the art to which the present invention pertains.

The compound of formula (1) of the present invention can be prepared characterized in that (a) a compound represented by the following formula (2):

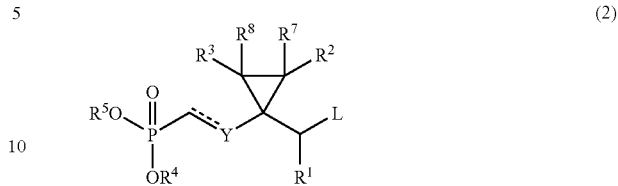

(2)

in which $R^1$, $R^2$, $R^3$, $R^4$, $R^5$, $R^7$, $R^8$ and Y are defined as previously described, and L represents a leaving group, preferably methanesulfonyloxy, p-toluenesulfonyloxy or halogen, is reacted with a compound represented by the following formula (3):

QH (3)

in which Q is defined as previously described, to produce the compound of formula (1), (b) a compound represented by the following formula (9):

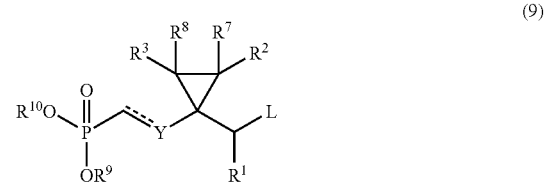

(9)

in which $R^1$, $R^2$, $R^3$, $R^7$, $R^8$, Y and L are defined as previously described, and $R^9$ and $R^{10}$ independently of one another represent optionally substituted alkyl, is reacted with the compound of formula (3) to produce a compound represented by the following formula (10):

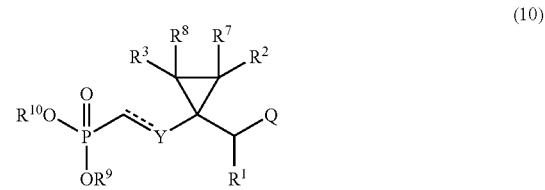

(10)

in which $R^1$, $R^2$, $R^3$, $R^7$, $R^8$, Y, Q, $R^9$ and $R^{10}$ are defined as previously described, and the resulting compound of formula (10) is hydrolyzed in the presence of a Lewis acid to produce a compound represented by the following formula (1a):

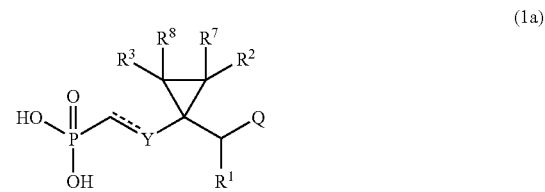

(1a)

in which $R^1$, $R^2$, $R^3$, $R^7$, $R^8$, Y and Q are defined as previously described, or (c) groups $R^{4'}$ and $R^{5'}$ are introduced into the compound of formula (1a) to produce a compound represented by the following formula (1b):

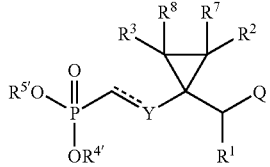
(1b)

in which $R^1$, $R^2$, $R^3$, $R^7$, $R^8$, Y and Q are defined as previously described, and $R^{4'}$ and $R^{5'}$ represent $R^4$ and $R^5$ with the exception of hydrogen, respectively, or further the compounds thus obtained are subjected to conventional conversions (see: U.S. Pat. Nos. 6,037,335, 5,935,946, and 5,792,756).

In the above process variants (a) to (c) for preparing the compound of formula (1), the reactions may be carried out in a solvent and in the presence of a base. As the solvent, one or more selected from a group consisting of dimethylformamide, dichloromethane, tetrahydrofuran, chloroform, 1-methyl-2-pyrrolidinone and dimethylacetamide can be mentioned, and as the base one or more selected from a group consisting of sodium hydride, sodium carbonate, potassium carbonate, sodium bicarbonate, potassium bicarbonate, potassium t-butoxide, hydrogen bis(trimethylsilyl)amide, sodium amide, cesium carbonate and potassium bis(trimethylsilyl)amide can be mentioned. The Lewis acid which can be used in the process variant (b) includes trimethylsilylhalide. Further, in the process variant (c) for introducing the groups $R^{4'}$ and $R^{5'}$ into the compound of formula (1a), this compound is subjected to an ether-forming reaction with an alkylhalide in the presence of a base, or is treated with thionyl chloride, oxalyl chloride or phosphorus pentachloride to produce a dichlorophosphonate derivative which is then reacted with a suitable alcohol or amine to give the desired compound.

The phosphonate compound of formula (2) used as a starting material in the above process is itself a novel compound. Therefore, it is another object of the present invention to provide the compound of formula (2).

The compound of formula (2) wherein Y is O, $R^1$ is hydrogen, and each of $R^2$, $R^3$, $R^7$ and $R^8$ is hydrogen or alkyl, that is, a compound of the following formula (8), can be prepared characterized in that (i) an ethylglycolate, the alcohol group of which is protected, represented by the following formula (4):

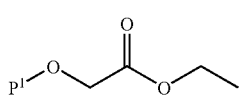
(4)

in which $P^1$ represents an alcohol-protecting group, preferably benzyl (Bn), tetrahydropyranyl (THP), t-butyldiphenylsilyl (TBDPS), or t-butyldimethylsilyl (TBDMS), is reacted with ethyl magnesium bromide[$C_2H_5MgBr$] or the corresponding alkyl magnesium bromide or alkyl magnesium chloride in the presence of titanium tetraisopropoxide[Ti(OiPr)$_4$], (ii) the resulting cyclopropanol represented by the following formula (5):

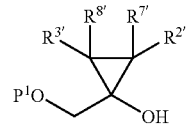
(5)

in which $P^1$ is defined as previously described and each of $R^{2'}$, $R^{3'}$, $R^{7'}$ and $R^{8'}$ represents hydrogen or alkyl, is subjected to an ether-forming reaction in the presence of a base with a compound represented by the following formula (6):

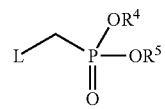
(6)

in which L, $R^4$ and $R^5$ are defined as previously described, to produce a phosphonate compound represented by the following formula (7):

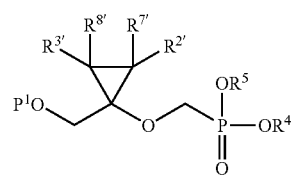
(7)

in which $P^1$, $R^{2'}$, $R^{3'}$, $R^{7'}$, $R^{8'}$, $R^4$ and $R^5$ are defined as previously described, and (iii) the alcohol-protecting group of the resulting compound of formula (7) is removed and a leaving group (L) is introduced to produce a compound represented by the following formula (8):

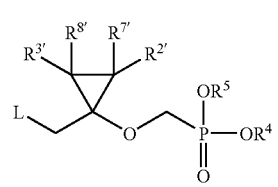
(8)

in which L, $R^{2'}$, $R^{3'}$, $R^{7'}$, $R^{8'}$, $R^4$ and $R^5$ are defined as previously described.

The process for preparing the simplest compound of formula (8) (that is, all of $R^{2'}$, $R^{3'}$, $R^{7'}$ and $R^{8'}$ are hydrogen) is briefly depicted in the following Reaction Scheme 1:

Reaction Scheme 1

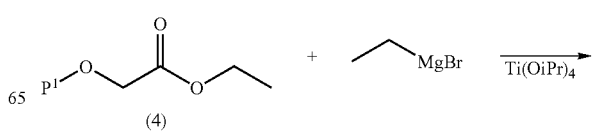
(4)

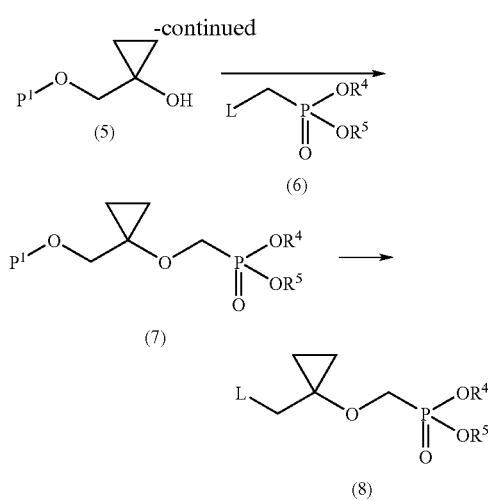

The specific reaction conditions of the above process can be referred to the following Preparations and Examples.

Further, the compound of formula (2) wherein Y is —$CH_2$—, and each of $R^1$, $R^2$, $R^3$, $R^7$ and $R^8$ is hydrogen, that is a compound of the following formula (11):

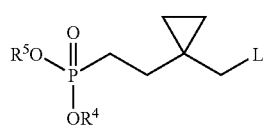

(11)

in which L, $R^4$ and $R^5$ are defined as previously described, can be prepared by a process as depictd in the following Reaction Scheme 2:

Reaction Scheme 2 is briefly explained below. (i) According to a known method (see: JOC, 1975, Vol. 40, 2969-2970), dialkylmalonate is reacted with dihaloethane to give malonic acid wherein cyclopropyl group is introduced into its 2-position. (ii) The malonic acid is reduced to give diol compound, one hydroxy group of which is then protected with a suitable protecting group ($P^1$ is defined as previously described). Then, the other hydroxy group is oxidized to an aldehyde group. (iii) The resulting aldehyde compound is reacted with tetraalkylmethylenediphosphonate to give the desired phosphonate compound. (iv) The phosphonate compound thus obtained is reduced to give a compound having no unsaturated bond, alcohol-protecting group ($P^1$) is removed, and a leaving group (L) is introduced to give the compound of formula (11).

Further, the compound of formula (2) wherein Y is —$N(CH_3)$— and each of $R^1$, $R^2$, $R^3$, $R^7$ and $R^8$ is hydrogen, that is a compound of the following formula (12):

(12)

in which L, $R^4$ and $R^5$ are defined as previously described, can be prepared by a process as depictd in the following Reaction Scheme 3:

Reaction Scheme 2

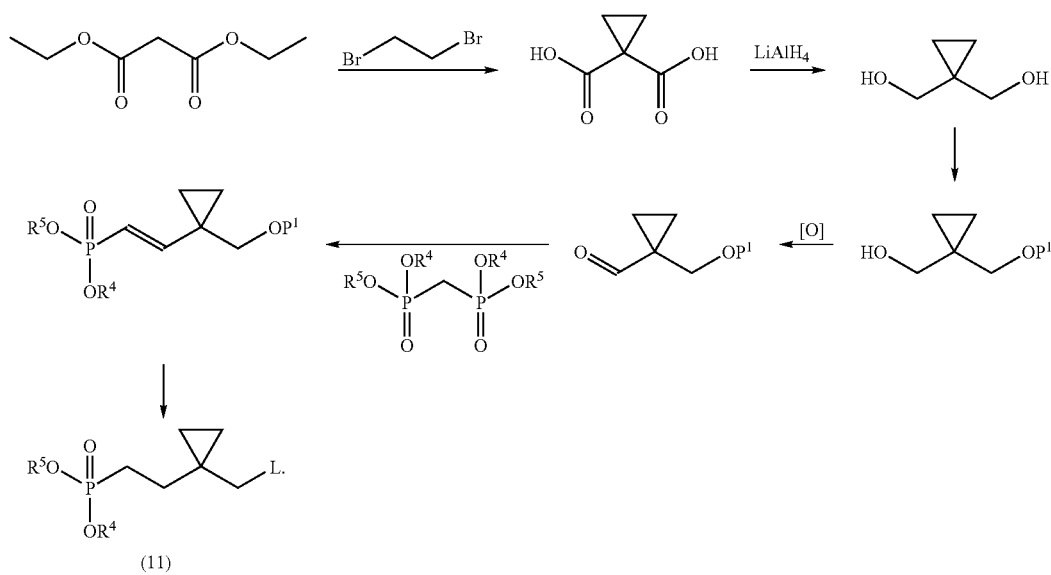

Reaction Scheme 3

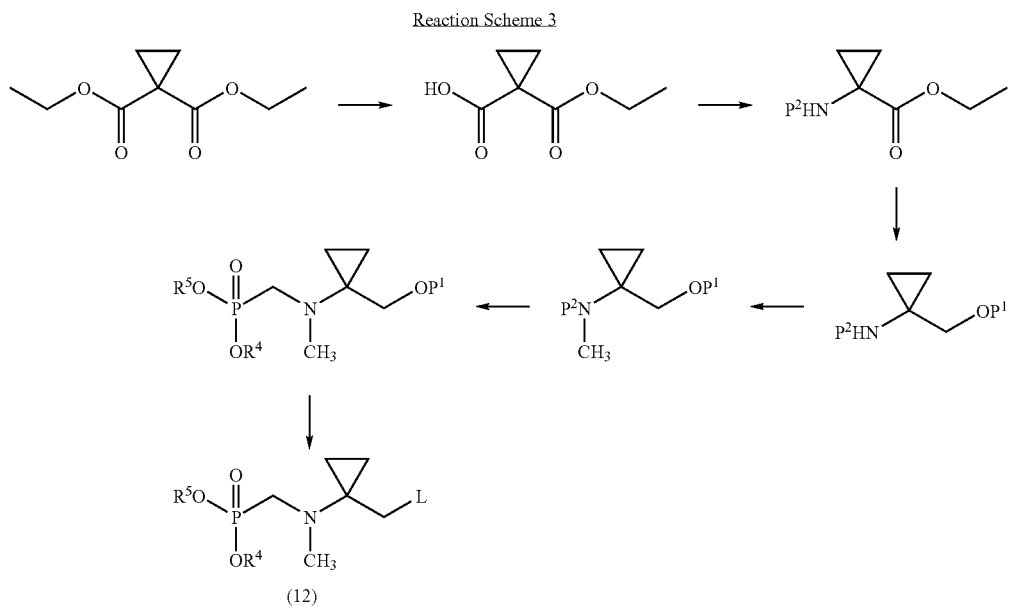

Reaction Scheme 3 is briefly explained below. (i) Diethyl 1,1-cyclopropyl dicarboxylate is selectively hydrolyzed to give a monocarboxylic acid. (ii) An amine group is introduced into the monocarboxylic acid according to the known Curtious Reaction (see: S. Linke, G. T. Tisue and W. Lowowski, J. Am. Chem. Soc. 1967, 89, 6308). (iii) The amine group is protected with a suitable protecting group [$P^2$ may be carbamate or various benzyl protecting groups, or alkyl group (methyl, ethyl, etc.)]. (iv) The opposite ester group is reduced into a hydroxy group, which is then protected ($P^1$ is defined as previously described). (v) The compound protected with protecting groups is reacted with methyl iodide in the presence of sodium hydride to introduce methyl group into the amine group. (vi) The amine-protecting group is removed and the resulting compound is reacted with dialkylbromomethylphosphonate to give the desired phosphonate compound. (vii) The alcohol-protecting group ($P^1$) is removed from the phosphonate compound thus obtained and then a leaving group (L) is introduced to give the compound of formula (12).

The specific reaction conditions of the above processes can be referred to the following Preparations and Examples.

After the reaction is completed, the resulting product may be further separated and purified by usual work-up processes, such as for example, chromatography, recrystallization, etc.

The compound of formula (1) of the present invention can be effectively used as an antiviral agent. Therefore, it is another object of the present invention to provide a composition for the treatment of viral diseases, which comprises as an active ingredient the compound of formula (1), pharmaceutically acceptable salt, hydrate, solvate or isomer thereof together with the pharmaceutically acceptable carrier.

When the active compound according to the present invention is used for clinical purpose, it is preferably administered in an amount ranging generally from 0.1 to 10000 mg, preferably from 0.5 to 100 mg per kg of body weight a day. The total daily dosage may be administered in once or over several times. However, the specific administration dosage for the patient can be varied with the specific compound used, body weight, sex or hygienic condition of the subject patient, diet, time or method of administration, excretion rate, mixing ratio of the agent, severity of the disease to be treated, etc.

The compound of the present invention may be administered in the form of injections or oral preparations.

Injections, for example, sterilized aqueous or oily suspension for injection, can be prepared according to the known procedure using suitable dispersing agent, wetting agent, or suspending agent. Solvents which can be used for preparing injections include water, Ringer's fluid and isotonic NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent and binding agent.

When the compound according to the present invention is clinically applied for obtaining the desired antiviral effect, the active compound of formula (1) can be administered in combination with one or more substances selected from the known anti-cancer or antiviral agents. As the anti-cancer or antiviral agents which can be administered together with the compound of the present invention in such a manner, 5-Fluorouracil, Cisplatin, Doxorubicin, Taxol, Gemcitabine, Lamivudine, etc. can be mentioned.

However, preparations comprising the compound of the present invention are not restricted to those explained above, but may contain any substances useful for the treatment or prevention of cancers or viral diseases.

The present invention will be more specifically explained in the following Examples and Experiments. However, it should be understood that these Examples and Experiments are intended to illustrate the present invention but not in any manner to limit the scope of the present invention.

Preparation 1

Synthesis of 1-({[t-butyl(diphenyl)silyl]oxy}methyl)cyclopropanol

According to the description in a reference (see: *Syn. Lett.* 07, 1053-1054, 1999), the title compound was prepared as follows. 12 g (35 mmole) of ethyl 2-{[t-butyl(diphenyl)silyl]oxy}acetate was dissolved in 200 ml of tetrahydrofuran (THF) and 2.2 ml of titaniumtetraisopropoxide was added thereto. To the mixture was slowly added 29.2 ml of ethylmagnesiumbromide (3.0M in THF), and the reaction solution was stirred for 12 hours at room temperature. 20 ml of saturated ammonium chloride was added to stop the reaction. About 150 ml of tetrahydrofuran (THF) used as a solvent was removed by distillation under reduced pressure, and the reaction mixture was extracted twice with 200 ml of ethyl acetate. The ethyl acetate extract was distilled under reduced pressure to give 11.4 g (Yield 100%) of the title compound as a white solid.

$^1$H NMR (CDCl$_3$) δ 0.44 (q, 2H), 0.78 (q, 2H), 1.09 (s, 9H), 3.67 (s, 2H), 7.41 (m, 6H), 7.70 (m, 4H)
ESI: 344 (M+NH$_4$)$^+$, C20H26O2Si

Preparation 2

Synthesis of diisopropyl{[1-({[t-butyl(diphenyl)silyl]oxy}methyl)cyclopropyl]oxy}methylphosphonate The compound prepared in Preparation 1 (6.5 g) was dissolved in 10 ml of dimethylformamide (DMF), 32 ml of lithium t-butoxide (1.0M in THF) was added thereto, and the resulting mixture was stirred for 10 minutes. To the mixture was added 7.0 g of diisopropyl bromomethylphosphonate, and then the temperature was raised to 40° C. and the mixture was stirred for 4 hours. Dimethylformamide (DMF) was removed by distillation under reduced pressure, 40 ml of saturated ammonium chloride was added to the residue, which was then extracted with ethyl acetate. The ethyl acetate extract was distilled under reduced pressure and the residue was purified by silica gel column chromatography (eluent: ethyl acetate/n-hexane=1/1, v/v) to give 6.8 g (Yield 70%) of the title compound.

$^1$H NMR (CDCl$_3$) δ 0.53 (m, 2H), 0.88 (m, 2H), 1.07 (s, 9H), 1.29 (t, 12H), 3.78 (s, 2H), 3.98 (d, 6H), 4.75 (m, 2H), 7.40 (m, 6H), 7.67 (m, 4H)

Preparation 3

Synthesis of diisopropyl{1-[(hydroxymethyl)cyclopropyl]oxy}methylphosphonate

The compound prepared in Preparation 2 (8.3 g) was dissolved in 100 ml of methanol, 3.1 g of ammonium fluoride was added thereto, and the resulting mixture was heated under reflux for 2 hours. After the reaction was completed, methanol was removed by distillation under reduced pressure and the residue was purified by silica gel column chromatography (eluent: dichloromethane/methanol=20/1, v/v) to give 3.6 g (Yield 82%) of the title compound.

$^1$H NMR (CDCl$_3$) δ 0.60 (t, 2H), 0.87 (t, 2H), 1.28 (d, 12H), 2.5 (br s, 1H), 3.65 (s, 2H), 3.83 (d, 2H), 4.82 (m, 2H)
ESI: 267 (M+1)$^+$, C11H23O4P

Preparation 4

Synthesis of {1-[(diisopropoxyphosphoryl)methoxy]cyclopropyl}methylmethane-sulfonate The compound prepared in Preparation 3 (1.5 g) was dissolved in 50 ml of dichloromethane, 0.85 ml of triethylamine and 0.84 g of methanesulfonylchloride were added thereto, and the resulting mixture was stirred for 30 minutes at room temperature. Saturated ammonium chloride was added to stop the reaction. The product was extracted with dichloromethane and the dichloromethane extract was concentrated by distillation under reduced pressure. The residue was purified by silica gel column chromatography (eluent: ethyl acetate/n-hexane=1/1, v/v) to give 1.63 g (Yield 81%) of the title compound.

$^1$H NMR (CDCl$_3$) δ 0.77 (m, 2H), 1.09 (m, 2H), 1.32 (m, 12H), 3.10 (s, 3H), 3.82 (m, 2H), 4.33 (s, 2H), 4.71 (m, 2H)

Preparation 5

Synthesis of diisopropyl({1-[(6-amino-9H-purin-9-yl)methyl]cyclopropyl}oxy)methylphosphonate

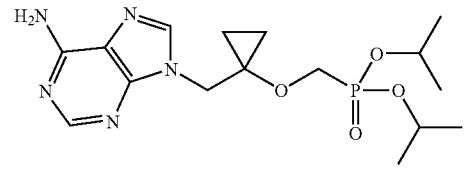

The compound prepared in Preparation 4 (430 mg) was dissolved in 18 ml of dimethylformamide, 57.6 mg (60% purity) of sodium hydride and 162 mg of adenine were added thereto, and the resulting mixture was heated under reflux over 4 hours. Saturated ammonium chloride was added to stop the reaction. The product was extracted with ethyl acetate, and the ethyl acetate extract was distilled under reduced pressure. The residue was purified by silica gel column chromatography (eluent: dichloromethane/methanol=20/1, v/v) to give 201 mg (Yield 44%) of the title compound.

$^1$H NMR (CDCl$_3$) δ 0.86 (t, 2H), 1.01 (t, 2H), 1.24 (d, 6H), 1.34 (d, 6H), 3.86 (d, 2H), 4.34 (s, 2H), 4.71 (m, 2H), 5.97 (br s, 2H), 8.32 (s, 1H), 8.58 (s, 1H)
ESI: 384 (M+1)$^+$, C16H25N5O4P

Preparation 6

Synthesis of diisopropyl({1-[(2-amino-6-chloro-9H-purin-9-yl)methyl]cyclopropyl}oxy)methylphosphonate

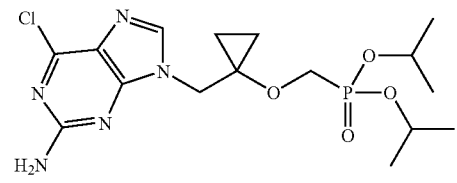

The compound prepared in Preparation 4 (1.64 g) was dissolved in 70 ml of dimethylformamide, 219 mg (60% purity) of sodium hydride and 773 mg of 2-amino-6-chloro-9H-purine were added thereto, and the resulting mixture was stirred for 4 hours while heating at a temperature of up to 80° C. Saturated ammonium chloride was added to stop the reaction. The product was extracted with ethyl acetate, and the ethyl acetate extract was distilled under reduced pressure. The residue was purified by silica gel column chromatography (eluent: dichloromethane/methanol=20/1, v/v) to give 765 mg (Yield 40%) of the title compound.

$^1$H NMR (CDCl$_3$) δ 0.80 (t, 2H), 1.02 (t, 2H), 1.27 (d, 6H), 1.28 (d, 6H), 3.82 (d, 2H), 4.21 (s, 2H), 4.68 (m, 2H), 5.13 (br s, 2H), 8.15 (s, 1H)

ESI: 418 (M+1)$^+$, C16H25ClN5O4P

Preparation 7

Synthesis of diisopropyl[(1{[5-methyl-2,4-dioxo-3, 4-dihydro-1(2H)-pyrimidinyl]methyl}cyclopropyl) oxy]methylphosphonate

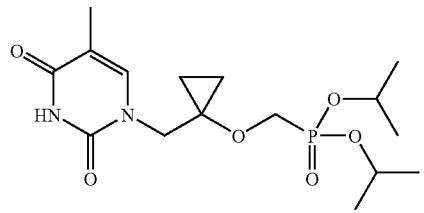

The compound prepared in Preparation 4 (118 mg) and thymine were reacted according to the same procedure as Preparation 6 to give 26 mg (Yield 21%) of the title compound.

$^1$H NMR (CDCl$_3$) δ 0.82 (t, 2H), 0.95 (t, 2H), 1.31 (m, 12H), 1.92 (s, 3H), 3.74 (d, 2H), 3.89 (s, 2H), 4.71 (m, 2H), 7.62 (s, 1H), 9.15 (s, 1H)

ESI: 375 (M+1)$^+$, C16H27N2O6P

Preparation 8

Synthesis of 1-({[t-butyl(diphenyl)silyl] oxy}methyl)-2-methylcyclopropanol

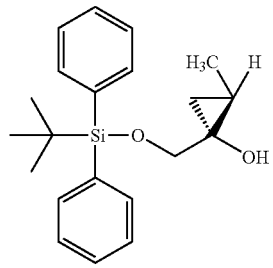

According to the description in a reference (see: *Syn. Lett.* 07, 1053-1054, 1999), the title compound was prepared as follows. 50 g (146 mmole) of ethyl 2-{[t-butyl(diphenyl)silyl]oxy}acetate was dissolved in 700 ml of tetrahydrofuran (THF) and 30.0 ml of titaniumtetraisopropoxide was added thereto. To the mixture was slowly added 290 ml of propylmagnesiumchloride (2.0M in THF) at −10° C., and the reaction solution was stirred for 12 hours at room temperature. 200 ml of saturated ammonium chloride was added to stop the reaction. The tetrahydrofuran (THF) used as a solvent was removed by distillation under reduced pressure, and the reaction mixture was extracted twice with 2000 ml of n-hexane. The n-hexane extract was distilled under reduced pressure and purified by silica gel column to give 42 g of the title compound.

$^1$H NMR (CDCl$_3$) δ 0.06 (t, 1H), 0.88 (dd, 2H), 0.97 (d, 3H), 1.09 (s, 9H) 1.1 (m, 1H), 2.78 (s, 1H), 3.70 (d, 1H), 3.86 (d, 1H), 7.41 (m, 6H), 7.70 (m, 4H)

ESI: 363 (M+Na)$^+$, C21H28O2Si

Preparation 9

Synthesis of diisopropyl{[1-({[t-butyl(diphenyl)silyl]oxy}methyl)-2-methylcyclopropyl] oxy}methylphosphonate

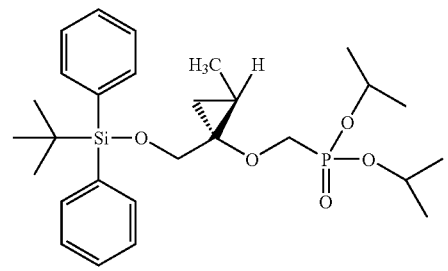

The compound prepared in Preparation 8 (4.2 g) was reacted according to the same procedure as Preparation 2 to give 3.3 g of the title compound.

$^1$H NMR (CDCl$_3$) δ 0.04 (t, 1H), 0.96 (dd, 1H), 0.97 (d, 3H), 1.05 (m, 1H), 1.06 (s, 9H), 1.23 (t, 12H), 3.72 (d, 1H), 3.95 (d, 2H), 3.98 (d, 1H), 4.75 (m, 2H), 7.40 (m, 6H), 7.68 (m, 4H)

Preparation 10

Synthesis of diisopropyl{1-[(hydroxymethyl)-2-methylcyclopropyl]oxy}methylphosphonate

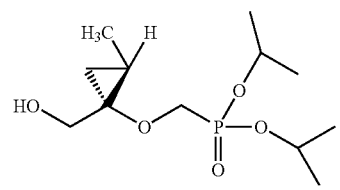

The compound prepared in Preparation 9 (3.3 g) was reacted according to the same procedure as Preparation 3 to give 1.7 g of the title compound.

$^1$H NMR (CDCl$_3$) δ 0.03 (t, 1H), 0.95 (dd, 1H), 0.96 (m, 1H), 1.11 (d, 3H), 1.35 (d, 12H), 2.17 (br s, 1H), 3.80 (d, 2H), 3.96 (d, 1H), 4.80 (m, 2H)

ESI: 303 (M+Na)$^+$, C12H22O5O4

Preparation 11

Synthesis of diisopropyl({1-[(6-amino-9H-purin-9-yl)methyl]-2-methylcyclopropyl}oxy)methylphosphonate

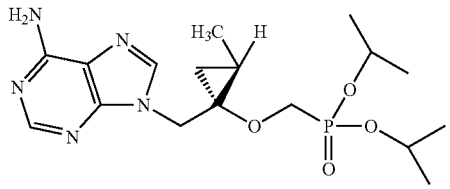

The compound prepared in Preparation 10 (1.5 g) was dissolved in 50 ml of dichloromethane, 0.85 ml of triethylamine and 0.84 g of methanesulfonylchloride were added thereto, and the resulting mixture was stirred for 30 minutes at room temperature. Saturated ammonium chloride was added to stop the reaction. The product was extracted with dichloromethane and the dichloromethane extract was concentrated by distillation under reduced pressure. The residue was used in the next reaction without any purification.

$^1$H NMR (CDCl$_3$) δ 0.42 (m, 1H), 1.12 (d, 3H), 1.25 (m, 1H), 1.32 (m, 12H), 1.33 (m, 1H), 3.10 (s, 3H), 3.76 (m, 2H), 4.31 (d, 1H), 4.71 (d, 1H), 4.76 (m, 2H)

The methanesulfonate thus obtained (430 mg) was dissolved in 18 ml of dimethylformamide, and 57.6 mg (60% purity) of sodium hydride and 162 mg of adenine were added thereto. The reaction mixture was refluxed under heating over 4 hours. Saturated ammonium chloride was added to stop the reaction. The product was extracted with ethyl acetate and the ethyl acetate extract was concentrated by distillation under reduced pressure. The residue was purified by silica gel column chromatography (eluent: dichloromethane/methanol=20/1, v/v) to give 201 mg (Yield 44%) of the title compound.

$^1$H NMR (CDCl$_3$) δ 0.53 (t, 1H), 1.13 (d, 3H), 1.15 (m, 1H), 1.30 (m, 12H), 1.41 (m, 1H), 1.85 (brs, 2H), 3.81 (m, 2H), 4.43 (m, 2H), 4.70 (m, 2H), 5.65 (br s, 2H), 8.26 (s, 1H), 8.34 (s, 1H)

ESI: 398 (M+1)$^+$, C17H28N5O4P

Preparation 12

Synthesis of diisopropyl({1-[(2-amino-6-chloro-9H-purin-9-yl)methyl]-2-methylcyclopropyl}oxy)methylphosphonate

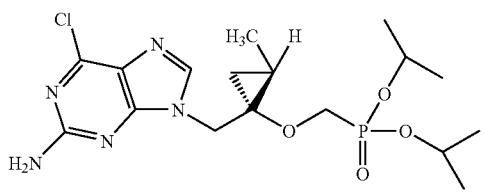

The compound prepared in Preparation 10 was reacted according to the same procedure as Preparation 11 except that 6-chloroguanine (2-amino-6-chloro-9H-purine) was used instead of adenine to give the title compound.

$^1$H NMR (CDCl$_3$) δ 0.47 (t, J=6.4 Hz, 1H), 1.12 (m, 4H), 1.24 (dd, J=2.8 Hz, 6.4 Hz, 6H), 1.28 (t, J=6.0 Hz, 6H), 1.38 (m, 1H), 3.80 (m, 2H), 4.28 (m, 2H), 4.68 (m, 2H), 5.13 (brs, 2H), 8.15 (s, 1H)

ESI: 432 (M+1)$^+$, C17H27ClN5O4P

Preparation 13

Synthesis of diisopropyl[(1{[5-methyl-2,4-dioxo-3,4-dihydro-1(2H)-pyrimidinyl]methyl}-2-methylcyclopropyl)oxy]methylphosphonate

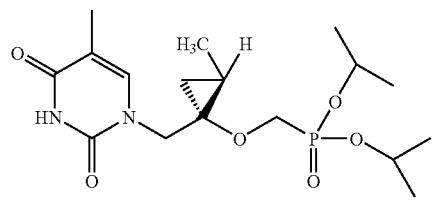

The compound prepared in Preparation 10 was reacted according to the same procedure as Preparation 11 except that thymine was used instead of adenine to give the title compound.

$^1$H NMR (CDCl$_3$) δ 0.48 (t, 1H), 1.10 (m, 4H), 1.24 (dd, 6H), 1.28 (t, J=6H), 1.38 (m, 1H), 1.92 (s, 3H), 3.80 (m, 2H), 4.28 (m, 2H), 4.68 (m, 2H), 7.62 (s, 1H), 9.15 (s, 1H)

ESI: 389 (M+1)$^{+'}$ C17H29N2O6P

Preparation 14

Synthesis of 1-(ethoxycarbonyl)cyclopropanecarboxylic acid

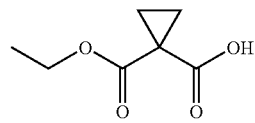

Diethyl 1,1-cyclopropane dicarboxylate (20 g) was hydrolyzed in 1N NaOH (107 ml) and ethanol (220 ml) for 16 hours, and the ethanol was removed by distillation under reduced pressure. The remaining starting material was removed by using ethyl acetate and the aqueous layer was acidified by 1N HCl. The reaction mixture was extracted with ethyl acetate and distilled under reduced pressure. The residue was purified by silica gel column to give the title compound in a yield of 94%.

$^1$H NMR (CDCl$_3$) δ 1.06 (t, 3H), 1.53 (m, 2H), 1.62 (m, 2H), 4.21 (q, 2H)

ESI: 159 (M+1)$^+$ C7H10O4

Preparation 15

Synthesis of ethyl 1-{[(benzyloxy)carbonyl]amino}cyclopropanecarboxylate

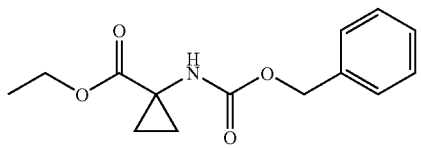

The carboxylic acid prepared in Preparation 14 (16 g) was dissolved in dichloromethane, 10.8 ml of oxalyl chloride was added dropwise, and 2 drops of dimethylformamide was added. The reaction mixture was stirred at room temperature for 3 hours and distilled under reduced pressure to give ethoxycarbonyl 1,1-cyclopropane carbonylchloride. This compound, not purified, was dissolved in 30 ml of dimethylformamide and the resulting solution was cooled with water-ice. 36 g of NaN$_3$ was added and the reaction was carried out at room temperature for 3 hours. The reaction solution was extracted with 100 ml of water and 200 ml of diethylether, and the diethylether extract was concentrated to give crude compound which was purified by silica gel column to give an azide compound.

$^1$H NMR (CDCl$_3$) δ 1.28 (t, 3H), 1.54 (m, 4H), 4.19 (q, 2H)

To the azide compound thus obtained (13 g) was added dropwise 11 ml of benzyl alcohol and the reaction mixture was heated to 100° C., by which the reactants were vigorously reacted with each other with the generation of gas. The reaction mixture was heated at 100° C. for further 1 hour, cooled to room temperature, and distilled under reduced pressure to remove benzyl alcohol. The residue was purified by silica gel column to give the title compound.

$^1$H NMR (CDCl$_3$) δ 1.19 (m, 5H), 1.54 (m, 2H), 4.11 (m, 2H), 5.15 (br.s, 2H), 7.32 (m, 5H)

Preparation 16

Synthesis of benzyl 1-{[t-butyl(diphenylsilyl)oxy]methylcyclopropyl}(methyl)carbamate

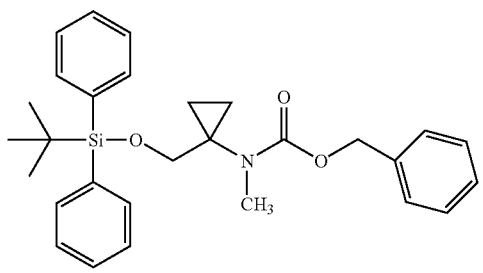

The carboxylate prepared in Preparation 15 (13.2 g) was dissolved in diethylether, to which 1.3 g of LiBH$_4$ dissolved in diethylether was slowly added dropwise. The reaction mixture was stirred at room temperature for 16 hours, and 50 ml of methanol and 5 ml of 1N HCl were added dropwise thereto. The reaction mixture was stirred for 2 hours, the precipitate was removed by suction filtration, and the solvent in the filtrate was removed by distillation under reduced pressure. The residue was purified by silica gel column to give benzyl 1-(hydroxymethyl)cyclopropylcarbamate.

This compound (9.3 g) was dissolved in dichloromethane, and 4.2 g of imidazole and 13.5 ml of t-butyldiphenylsilylchloride were added in order. The reaction mixture was stirred at room temperature for 4 hours and the solvent was removed by distillation under reduced pressure. The residue was purified by silica gel column to give benzyl 1-({[t-butyl(diphenyl)silyl]oxy}methyl)cyclopropylcarbamate.

$^1$H NMR (CDCl$_3$) δ 0.71-1.19 (m, 4H), 1.04 (s, 9H), 3.68 (br.s, 2H), 5.04 (s, 2H), 7.25-7.45 (m, 11H), 7.62 (d, 4H)

The carbamate thus obtained (5.5 g) was dissolved in THF, 3.5 ml of methane iodide (MeI) was added dropwise and then 1 g of NaH was added. The reaction mixture was stirred at room temperature for 4 hours and then extracted with 100 ml of diethylether and 100 ml of water. The diethylether extract was concentrated by distillation under reduced pressure and the residue was purified by silica gel column to give the title compound.

$^1$H NMR (CDCl$_3$) δ 0.78-0.84 (m, 4H), 1.03 (s, 9H), 3.03 (s, 3H), 3.55-3.80 (m, 2H), 5.10 (s, 2H), 7.24-7.45 (m, 11H), 7.61 (m, 4H)

Preparation 17

Synthesis of diisopropyl[1-({[t-butyl(diphenyl)silyl]oxy}methyl)cyclopropyl)(methyl)amino]methylphosphonate

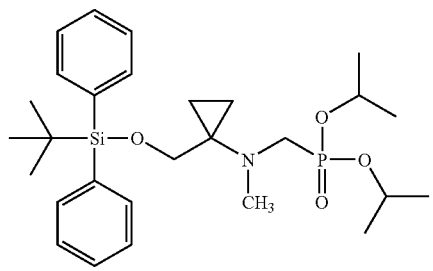

The carbamate prepared in Preparation 16 (1.0 g) was dissolved in ethanol, 100 mg of 10% Pd/C was added, and the reaction mixture was subjected to a hydrogenation under hydrogen atmosphere. After the reaction was completed, the solvent was removed by distillation under reduced pressure. The residue was purified by silica gel column to give 1-({[t-butyl(diphenyl)silyl]oxy}methyl)-N-methylcyclopropaneamine.

$^1$H NMR (CDCl$_3$) δ 0.36 (m, 2H), 0.65 (m, 2H), 1.05 (s, 9H), 2.36 (s, 3H), 3.57 (s, 2H), 7.37-7.45 (m, 11H), 7.66 (d, 4H)

The methylcyclopropaneamine thus obtained (1.0 g) was dissolved in dichloromethane, to which 1.03 ml of diisopropylethylamine and 1.3 ml of (diisopropyl phosphoryl)methyl trifluoromethansulfonate were added dropwise. The reaction mixture was reacted under stirring at room temperature for 4 hours, and then extracted with 100 ml of diethylether and 100 ml of water. The solvent in the diethylether extract was removed by distillation under reduced pressure and the residue was purified by silica gel column to give the title compound.

$^1$H NMR (CDCl$_3$) δ 0.42 (m, 2H), 0.69 (m, 2H), 1.04 (s, 9H), 1.25 (d, 6H), 1.30 (d, 6H), 2.62 (s, 3H), 3.25 (d, 2H), 3.64 (s, 2H), 4.68 (m, 2H), 7.39 (m, 6H), 7.65 (d, 4H)

Preparation 18

Synthesis of diisopropyl(1-{[(6-amino-9H-purin-9-yl)methyl]cyclopropyl}(methyl)amino)methylphosphonate

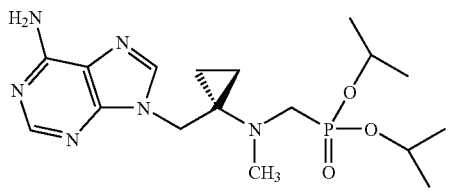

The compound prepared in Preparation 17 (0.32 g) was dissolved in methanol and 1.5 g of ammonium fluoride was added dropwise. The reaction mixture was reacted under stirring at 60° C. for 24 hours and then the solvent was removed by distillation under reduced pressure. The residue was purified by silica gel column to give methylaminediisopropylmethylphosphone 1,1-cyclopropane ethyl alcohol.

$^1$H NMR (CDCl$_3$) δ 0.56 (m, 2H), 0.73 (m, 2H), 1.31 (m, 12H), 2.56 (s, 3H), 3.11 (d, 2H), 3.55 (s, 2H), 4.70 (m, 2H)

The compound thus obtained was consecutively reacted according to the same procedure as Preparations 4 and 5 to give the title compound.

$^1$H NMR (CDCl$_3$) δ 0.78 (m, 2H), 0.86 (m, 2H), 1.25 (m, 12H), 2.35 (s, 3H), 4.10 (s, 2H), 4.68 (m, 2H), 5.13 (m, 2H), 8.32 (s, 1H), 8.58 (s, 1H)

ESI: 397 (M+1)$^+$, C17H29N6O3P

Preparation 19

Synthesis of diisopropyl(1-{[(2-amino-6-chloro-9H-purin-9-yl)methyl]cyclopropyl}(methyl)amino)methylphosphonate

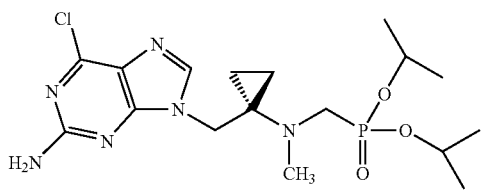

The compound prepared in Preparation 17 (0.32 g) was dissolved in methanol and 1.5 g of ammonium fluoride was added dropwise. The reaction mixture was reacted under stirring at 60° C. for 24 hours and then the solvent was removed by distillation under reduced pressure. The residue was purified by silica gel column to give methylaminediisopropylmethylphosphone 1,1-cyclopropane ethyl alcohol.

$^1$H NMR (CDCl$_3$) δ 0.56 (m, 2H), 0.73 (m, 2H), 1.31 (m, 12H), 2.56 (s, 3H), 3.11 (d, 2H), 3.55 (s, 2H), 4.70 (m, 2H)

The compound thus obtained was consecutively reacted according to the same procedure as Preparations 4 and 6 to give the title compound.

$^1$H NMR (400 MHz, CD$_3$OD): δ 0.79 (m, 2H), 0.89 (m, 2H), 1.26 (m, 12H), 2.38 (s, 3H), 2.76 (d, 2H, J=7 Hz), 4.11 (s, 2H), 4.65 (m, 2H), 5.13 (m, 2H), 8.02 (s, 1H)

ESI: 431 (M+1)$^+$, C17H28ClN6O3P

Preparation 20

Synthesis of diisopropyl[(1-{[5-methyl-2,4-dioxo-3,4-dihydro-1(2H)-pyrimidinyl]methyl}cyclopropyl)(methyl)amino]methylphosphonate

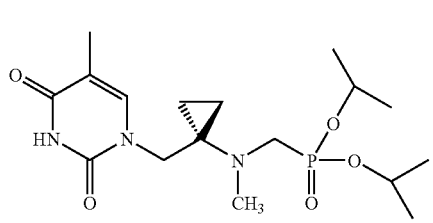

The compound prepared in Preparation 17 (0.32 g) was dissolved in methanol and 1.5 g of ammonium fluoride was added dropwise. The reaction mixture was reacted under stirring at 60° C. for 24 hours and then the solvent was removed by distillation under reduced pressure. The residue was purified by silica gel column to give methylaminediisopropylmethylphosphone 1,1-cyclopropane ethyl alcohol.

$^1$H NMR (CDCl$_3$) δ 0.56 (m, 2H), 0.73 (m, 2H), 1.31 (m, 12H), 2.56 (s, 3H), 3.11 (d, 2H), 3.55 (s, 2H), 4.70 (m, 2H)

The compound thus obtained was consecutively reacted according to the same procedure as Preparations 4 and 7 to give the title compound.

$^1$H NMR (CDCl$_3$) δ 0.79 (m, 2H), 0.90 (m, 2H), 1.31 (m, 12H), 1.92 (s, 3H), 2.38 (s, 3H), 3.75 (d, 2H), 4.10 (s, 2H), 4.65 (m, 2H), 7.62 (s, 1H), 9.15 (s, 1H)

Preparation 21

Synthesis of 1,1-cyclopropanedicarboxylic acid

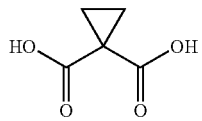

In 50% NaOH 187 ml was dissolved 15 g of diethylmalonate at room temperature. Benzyltriethylammoniumchloride (21.3 g) was added and the resulting mixture was stirred for 10 minutes. 1,2-Dibromoethane (12.3 g) was added to the reaction solution and the resulting mixture was stirred for more than 18 hours at room temperature. The reaction mixture was neutralized by adding dropwise conc. sulfuric acid and then extracted with ethyl acetate. The extract was distilled under reduced pressure to give 6.2 g of the title compound as a white solid.

$^1$H NMR (CDCl$_3$) δ 1.88 (s, 4H)

Preparation 22

Synthesis of [1-({[t-butyl(diphenyl)silyl]oxy}methyl)cyclopropyl]methanol

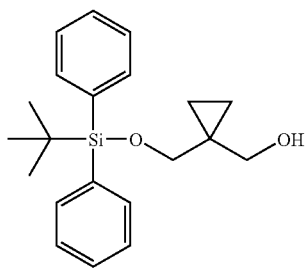

Lithium aluminum hydride (LAH) 15.3 g was dissolved in 39 g of tetrahydrofuran, and 11.7 g of the carboxylic acid prepared in Preparation 21 was slowly added dropwise at 0° C. The reaction solution was refluxed for 17 hours. The reaction was stopped by adding 10% HCl at room temperature and the mixture was extracted with ethyl acetate. The extract was distilled under reduced pressure and the residue was purified by silica gel column to give 8.2 g of diol compound.

$^1$H NMR (CDCl$_3$) δ 0.56 (s, 4H), 2.22 (s, 2H), 3.63 (s, 4H)

The compound thus obtained (400 mg) was dissolved in 12 ml of THF, 184 mg of NaH and 1.16 g of t-butyldiphenylsilylchloride (TBDPSCl) were added, and the resulting mixture was refluxed for 6 hours. The reaction was stopped by adding 10 ml of water and the mixture was extracted with ethyl acetate. The extract was distilled under reduced pressure and the residue was purified by silica gel column to give 1.1 g of the title compound.

$^1$H NMR (CDCl$_3$) δ 0.33 (t, 2H), 0.48 (t, 2H), 1.23 (s, 9H), 3.59 (d, 4H), 7.42 (m, 6H), 7.68 (m, 4H)

Preparation 23

Synthesis of diethyl(E)-2-[1-({[t-butyl(diphenyl)silyl]oxy}methyl)cyclopropyl]ethenylphosphonate

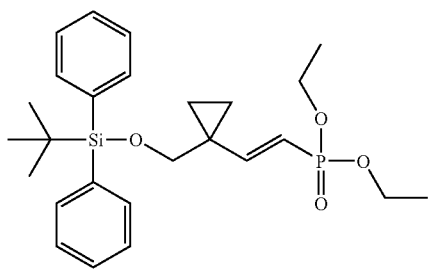

The compound prepared in Preparation 22 (2 g) was dissolved in 50 ml of dichloromethane, and 1.03 g of N-methylmorpholine N-oxide and 103 mg of tetrapropylammoniumperruthenate (TPAP) were added thereto at room temperature. The reaction mixture was stirred for about 1 hour at room temperature and the reaction was stopped by adding 20 ml of water. The reaction solution was extracted with dichloromethane and the extract was concentrated under reduced pressure to give 2.0 g of aldehyde compound.

$^1$H NMR (CDCl$_3$) δ 1.03 (s, 9H), 1.04 (t, 2H), 1.05 (t, 2H), 3.94 (s, 2H), 7.37 (m, 6H), 7.64 (m, 4H), 9.10 (s, 1H)

Tetraethylmethylene diphosphonate (1.7 g) was dissolved in 60 ml of tetrahydrofuran (THF). At −78° C., 264 mg of NaH was added, the resulting mixture was stirred for 20 minutes, and then 1.9 g of the aldehyde compound as obtained above was added. The reaction solution was stirred at room temperature for 1 hour, and the reaction was stopped by adding 20 ml of water. The reaction solution was extracted with ethyl acetate and the extract was concentrated under reduced pressure. The residue was purified by silica gel column to give 2.32 g of the title compound.

$^1$H NMR (CDCl$_3$) δ 0.76 (t, 2H), 0.81 (t, 2H), 1.04 (s, 9H), 1.31 (t, 6H), 3.71 (s, 2H), 4.05 (m, 4H), 5.70 (m, 1H), 6.42 (m, 1H), 7.43 (m, 6H), 7.64 (d, 4H)

ESI: 501 (M+1)$^{+}$ C28H41O4PSi

Preparation 24

Synthesis of diethyl 2-[1-(hydroxymethyl)cyclopropyl]ethenylphosphonate

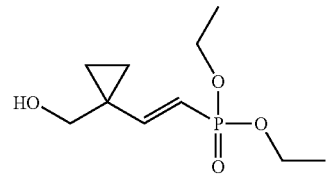

The compound prepared in Preparation 23 was reacted according to the same procedure as Preparation 3 to give the title compound.

$^1$H NMR (CDCl$_3$) δ 0.76 (t, 2H), 0.81 (t, 2H), 1.04 (s, 9H), 1.31 (t, 6H), 3.71 (s, 2H), 4.05 (m, 4H), 5.70 (m, 1H), 6.42 (m, 1H), 7.43 (m, 6H), 7.64 (d, 4H)

ESI: 501 (M+1)$^{+}$ C28H41O4PSi

Preparation 25

Synthesis of diethyl 2-{1-[(6-amino-9H-purin-9-yl)methyl]cyclopropyl}ethenylphosphonate

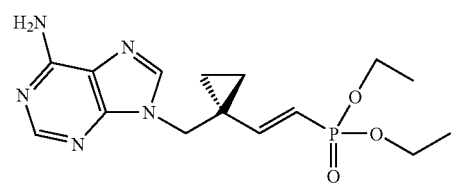

The compound prepared in Preparation 24 was reacted according to the same procedure as Preparations 4 and 5 to give the title compound.

$^1$H NMR (CDCl$_3$) δ 1.07 (t, 2H), 1.19 (t, 2H), 1.22 (t, 6H), 3.93 (s, 4H), 4.33 (s, 2H), 5.55 (s, 2H), 5.63 (m, 1H), 6.49 (m, 1H), 7.88 (s, 1H), 8.37 (s, 1H)

ESI: 352 (M+1)$^{+}$ C15H22N5O3P

Preparation 26

Synthesis of diethyl 2-{1-[(2-amino-6-chloro-9H-purin-9-yl)methyl]cyclopropyl}ethenylphosphonate

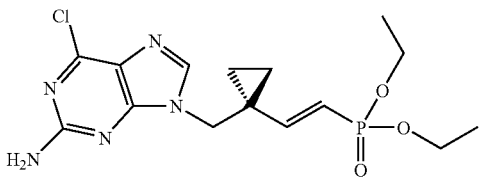

The compound prepared in Preparation 24 was reacted according to the same procedure as Preparations 4 and 6 to give the title compound.

$^1$H NMR (CDCl$_3$) δ 1.06 (t, 2H), 1.15 (t, 2H), 1.23 (t, 6H), 3.93 (s, 4H), 4.18 (s, 2H), 5.12 (s, 2H), 5.59 (m, 1H), 6.58 (m, 1H), 7.81 (s, 1H)

ESI: 386 (M+1)$^{+'}$ C15H21ClN5O3P

Preparation 27

Synthesis of diethyl 2-(1-{[5-methyl-2,4-dioxo-3,4-dihydro-1(2H)-pyrimidinyl]methyl}cyclopropyl)ethenylphosphonate

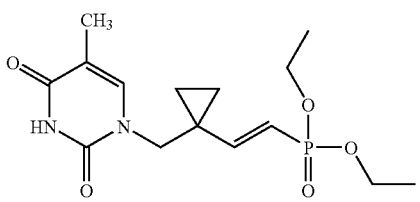

The compound prepared in Preparation 24 was reacted according to the same procedure as Preparations 4 and 7 to give the title compound.

$^1$H NMR (CDCl$_3$) δ 0.93 (t, 2H), 1.01 (t, 2H), 1.24 (t, 6H), 1.92 (s, 3H), 3.91 (s, 2H), 3.96 (m, 4H), 5.49 (m, 1H), 5.87 (m, 1H), 7.62 (s, 1H). 9.15 (s, 1H)

ESI: 343 (M+1)$^{+'}$ C15H23N2O5P

Preparation 28

Synthesis of 1-({[t-butyl(diphenyl)silyl]oxy}methyl)-2,2-dimethylcyclopropanol

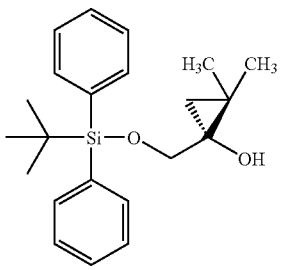

According to the description in a reference (see: *Syn. Lett.* 07, 1053-1054, 1999), the title compound was prepared as follows. 10 g (29 mmole) of ethyl 2-{[t-butyl(diphenyl)silyl]oxy}acetate was dissolved in 100 ml of tetrahydrofuran (THF) and 6.0 ml of titaniumtetraisopropoxide was added thereto. To the mixture was slowly added 37 ml of isobutylmagnesiumbromide (2.0M in THF) at −10° C., and the reaction solution was stirred for 12 hours at room temperature. 50 ml of saturated ammonium chloride was added to stop the reaction. The tetrahydrofuran (THF) used as a solvent was removed by distillation under reduced pressure, and the reaction mixture was extracted twice with 500 ml of n-hexane. The n-hexane extract was distilled under reduced pressure and purified by silica gel column to give 5.0 g of the title compound.

$^1$H NMR (CDCl$_3$) δ 0.25 (d, 1H), 0.51 (d, 2H), 0.99 (s, 3H), 1.07 (s, 9H), 1.22 (s, 3H), 3.71 (d, 1H), 3.91 (d, 1H), 7.41 (m, 6H), 7.70 (m, 4H)

ESI: 355 (M+1)$^+$, C22H30O2Si

Preparation 29

Synthesis of diisopropyl{[1-({[t-butyl(diphenyl)silyl]oxy}methyl)-2,2-dimethylcyclopropyl]oxy}methylphosphonate

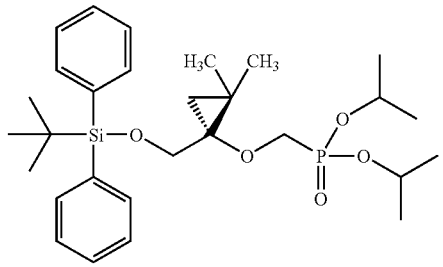

The compound prepared in Preparation 28 was reacted according to the same procedure as Preparation 2 to give the title compound.

$^1$H NMR (CDCl$_3$) δ 0.29 (d, 1H), 0.60 (d, 1H), 1.06 (s, 3H), 1.09 (s, 9H), 1.27 (s, 3H), 1.30 (m, 12H), 3.75 (m, 2H), 3.92 (m, 2H), 4.72 (m, 2H), 7.41 (m, 6H), 7.67 (m, 4H)

ESI: 519 (M+1)$^+$, C28H43O5PSi

Preparation 30

Synthesis of diisopropyl{1-[(hydroxymethyl)-2,2-dimethylcyclopropyl]oxy}methylphosphonate

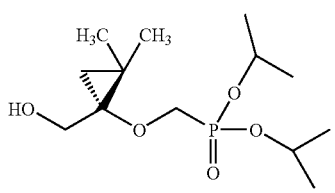

The compound prepared in Preparation 29 was reacted according to the same procedure as Preparation 3 to give the title compound.

$^1$H NMR (CDCl$_3$) δ 0.39 (d, 1H), 0.59 (d, 1H), 1.13 (s, 3H), 1.21 (s, 3H), 1.33 (d, 12H), 3.76 (m, 2H), 3.86 (m, 2H), 4.76 (m, 2H)

ESI: 295 (M+1)$^+$, C13H27O4P

Preparation 31

Synthesis of diisopropyl({1-[(6-amino-9H-purin-9-yl)methyl]-2,2-dimethylcyclopropyl}oxy)methylphosphonate

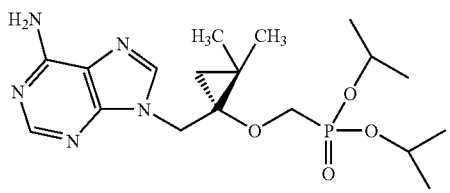

The compound prepared in Preparation 30 was reacted according to the same procedure as Preparation 11 to give the title compound.

$^1$H NMR (500 MHz, CDCl$_3$): δ 0.62 (d, J=5.9 Hz, 1H), 0.81 (d, J=5.9 Hz, 1H), 1.10 (s, 3H), 1.23 (m, 15H), 3.72 (dd, J=15.1, 11.0 Hz, 1H), 3.85 (dd, J=15.1, 5.5 Hz, 1H), 4.28 (d, J=15.1 Hz, 1H), 4.58 (d, J=15.1 Hz, 1H), 4.68 (m, 2H), 5.79 (bs, 2H), 8.19 (s, 1H), 8.32 (s, 1H)

ESI: 412 (M+1)$^+$, C18H30N5O4P

Preparation 32

Synthesis of diisopropyl({1-[(2-amino-6-iodo-9H-purin-9-yl)methyl]-2,2-dimethylcyclopropyl}oxy)methylphosphonate

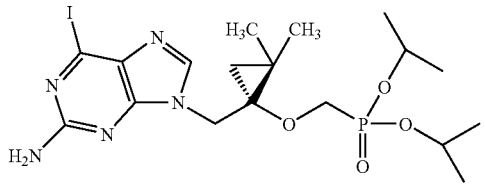

The compound prepared in Preparation 30 was reacted according to the same procedure as Preparation 12 except that 6-iodoguanine was used instead of 6-chloroguanine to give the title compound.

$^1$H NMR (500 MHz, CDCl$_3$): δ 0.58 (d, J=6.4 Hz, 1H), 0.80 (d, J=6.4 Hz, 1H), 1.10 (s, 3H), 1.24 (m, 8H), 3.72 (dd, J=13.0, 11.0 Hz, 1H), 3.88 (dd, J=13.0, 9.3 Hz, 1H) 4.08 (d, J=15.1 Hz, 1H), 4.47 (d, J=15.1 Hz, 1H), 4.67 (m, 2H), 5.05 (bs, 1H), 8.10 (s, 1H)

ESI: 538 (M+1)$^+$, C18H29IN5O4P

Preparation 33

Synthesis of diisopropyl[(1{[5-methyl-2,4-dioxo-3,4-dihydro-1(2H)-pyrimidinyl]methyl}-2,2-dimethylcyclopropyl)oxy]methylphosphonate

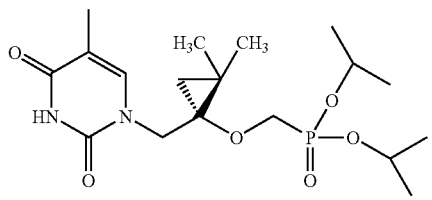

The compound prepared in Preparation 30 was reacted according to the same procedure as Preparation 13 to give the title compound.

$^1$H NMR (CDCl$_3$) δ 0.58 (d, 1H), 0.80 (d, 1H), 1.10 (s, 3H), 1.24 (dd, 6H), 1.28 (t, 6H), 1.58 (s, 3H), 1.92 (s, 3H), 3.72 (dd, 1H), 3.88 (dd, 1H), 4.08 (d, 1H), 4.47 (d, 1H), 4.67 (m, 2H), 7.62 (s, 1H), 9.15 (s, 1H)

ESI: 403 (M+1)$^+$ C18H31N2O6P

Preparation 34

Synthesis of 1-[1-({[t-butyl(diphenyl)silyl]oxy}methyl)cyclopropyl]-1-methyl alcohol

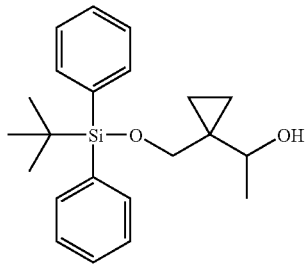

6 g of the compound prepared in Preparation 22 was dissolved in 150 ml of dichloromethane. 3.0 g of N-oxide and 103 mg of tetrapropylammoniumperruthenate (TPAP) were added thereto at room temperature. The reaction mixture was stirred for about 1 hour at room temperature and quenched by adding 20 ml of water. The reaction mixture was extracted with dichloromethane and the extract was concentrated under reduced pressure to give 6.0 g of aldehyde compound which went to next reaction without further purification.

5.23 g of the aldehyde was dissolved in 350 ml of THF. The solution was cooled to −78° C. and 10.3 ml of methylmagnesiumbromide (3.0M solution) was slowly added to the solution and then, stirred for 1 hour at room temperature. The reaction mixture was quenched by 0.5 ml of water and 0.5 ml of methanol and concentrated under reduced pressure. The residue was purified by silica gel column chromatography (eluent: ethyl acetate/n-hexane=1/8, v/v) to 3.57 g of title compound.

$^1$H NMR (CDCl$_3$) δ 0.22 (m, 1H), 0.39 (m, 2H), 0.61 (m, 1H), 1.06 (s, 9H), 1.24 (d, 3H), 3.3 (d, 1H), 3.47 (s, 2H), 3.9 (d, 1H), 7.43 (m, 6H), 7.64 (m, 6H)

Preparation 35

Synthesis of diethyl (E)-2-1-[1-({[t-butyl(diphenyl)silyl]oxy}methyl)cyclopropyl]-1-propenylphosphonate

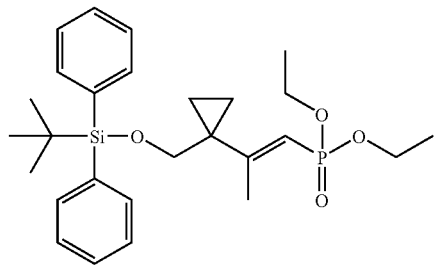

4 g of the compound prepared in preparation 34 was dissolved in 10 ml of dichloromethane. 2.1 g of n-morpholine N-oxide and 209 mg of tetrapropylammoniumperruthenate (TPAP) were added thereto at room temperature. The reaction mixture was stirred for about 1 hour at room temperature and quenched by adding 20 ml of water. The reaction mixture was extracted with dichloromethane and the extract was concentrated under reduced pressure to give 4.0 g of compound which went to next reaction without further purification.

Tetraethylmethylene diphosphonate (2.7 g) was dissolved in 30 ml of tetrahydrofuran (THF) at −78 and 4 ml of n-butyllithium was added. The resulting mixture was stirred for 20 minutes, and then 1.0 g of the ketone compound as obtained above was added. The reaction mixture was stirred at room temperature for 1 hour and was stopped by adding 20 ml of water. The reaction mixture was extracted with ethyl acetate and concentrated under reduced pressure. The residue was purified by silica gel column to give 654 mg of the title compound.

$^1$H NMR (CDCl$_3$) δ 0.58 (m, 1H), 0.69 (m, 2H), 1.02 (s, 9H), 1.20 (t, 6H), 2.09 (d, 3H), 3.59 (s, 2H), 4.05 (m, 4H), 5.61 (d, 1H), 7.38 (m, 6H), 7.63 (d, 4H)

Example 1

Synthesis of ({1-[(6-amino-9H-purin-9-yl)methyl]cyclopropyl}oxy)methylphosphonic acid (Compound 1)

The compound prepared in Preparation 5 (159 mg) was dissolved in 15 ml of dichloromethane, 1.27 g of trimethylsilylbromide was added thereto, and the resulting mixture was heated under reflux for 18 hours. After the completion of reaction, the reaction mixture was extracted with water, and the water extract was distilled under reduced pressure. The residue was purified by high performance liquid chromatography (HPLC) to give 0.89 g (Yield 90%) of the title compound as a white powder.

$^1$H NMR (MeOH-d4) δ 1.02 (d, 4H), 3.95 (d, 2H), 4.55 (s, 2H), 8.40 (s, 1H), 8.55 (s, 1H)

ESI: 300 (M+1)$^+$, C10H14N5O4P

Example 2

Synthesis of 3-[({1-[(6-amino-9H-purin-9-yl)methyl]cyclopropyl}oxy)methyl]-8,8-dimethyl-3,7-dioxo-2,4,6-trioxa-3$8^5$-phosphanon-1-yl pivalate (Compound 2)

The title compound was prepared according to the method known in a reference (see: J. Med. Chem., 37(12), 1857 (1994)) and U.S. Pat. No. 5,663,159 (1998).

The compound prepared in Example 1 (1.00 g) was dissolved in 150 ml of dry dimethylformamide, and 2.08 g (7.32 mmol) of N,N'-dicyclohexyl-4-morpholine-carboxamidine and 2.75 g (18.3 mmol) of chloromethyl pivalate were added thereto. When the reaction mixture became homogeneous after about 1 hour, it was stirred for 5 days at room temperature. The reaction solution was filtered, the filtrate was concentrated under reduced pressure, and the residue was fractionated with 50 ml of water and 50 ml of toluene to separate the organic layer. The aqueous layer was extracted twice with 50 ml of toluene. The combined organic layers were concentrated under reduced pressure. The residue was purified by column chromatography (eluent: methanol/dichloromethane=1/20, v/v) to give 0.59 g (Yield 32%) of the title compound as a white solid.

$^1$H NMR (500 MHz, CDCl$_3$) δ 0.91 (m, 2H), 1.12 (m, 2H), 1.20 (m, 18H), 1.90 (br s, 2H), 3.90 (d, 2H), 4.32 (s, 2H), 5.65 (m, 4H), 8.14 (s, 1H), 8.31 (s, 1H)

ESI: 528 (M+1)$^+$, C22H34N5O8P

Example 3

Synthesis of ({1-[(2-amino-6-chloro-9H-purin-9-yl)methyl]cyclopropyl}oxy)methyl phosphonic acid (Compound 3)

The compound prepared in Preparation 6 (73 mg) was reacted according to the same procedure as Example 1 to give 46 mg (Yield 80%) of the title compound.

$^1$H NMR (MeOH-d4) δ 1.00 (s, 2H), 1.07 (s, 2H), 3.94 (d, 2H), 4.52 (s, 2H), 9.50 (s, 1H)

ESI: 334 (M+1)$^+$, C10H13ClN5O4P

Example 4

Synthesis of ({1-[(2-amino-6-hydroxy-9H-purin-9-yl)methyl]cyclopropyl}oxy)methylphosphonic acid (Compound 5)

The compound prepared in Example 3 (41 mg) was dissolved in 5 ml of 2N hydrochloric acid and heated under reflux for 6 hours. Water was removed by distillation under reduced pressure to give 37 mg (Yield 95%) of the title compound as a white solid.

$^1$H NMR (MeOH-d4) δ 0.98 (m, 2H), 1.06 (m, 2H), 3.92 (d, 2H), 4.45 (s, 2H), 9.20 (s, 1H)

ESI: 316 (M+1)$^+$, C10H14N5O5P

Example 5

Synthesis of ({1-[(2-amino-9H-purin-9-yl)methyl]cyclopropyl}oxy)methylphosphonic acid (Compound 9)

The compound prepared in Preparation 6 (150 mg) was dissolved in 15 ml of tetrahydrofuran, 15 mg of 5% palladium/carbon was added thereto, and the compound was reduced under 1 atm of hydrogen atmosphere for 18 hours. After completion of reaction, palladium/carbon was removed by suction filtration and the filtrate was distilled under reduced pressure. The residue was purified by silica gel column chromatography (eluent: dichloromethane/methanol=20/1, v/v) to give 130 mg of diisopropyl compound (ESI: 384(M+1)$^+$, C16H26N5O4P). This compound was treated with trimethylsilylbromide according to the same procedure as Example 1 to give 91 mg (Yield 90%) of the title compound.

$^1$H NMR (MeOH-d4) δ 0.94 (m, 2H), 1.03 (m, 2H), 3.93 (d, 2H), 4.40 (s, 2H), 8.66 (s, 1H), 8.74 (s, 1H)

ESI: 300 (M+1)$^+$, C10H14N5O4P

Example 6

Synthesis of 3-[({1-[(2-amino-9H-purin-9-yl)methyl]cyclopropyl}oxy)methyl]-8,8-dimethyl-3,7-dioxo-2,4,6-trioxa-3$8^5$-phosphanon-1-yl pivalate (Compound 10)

The compound prepared in Example 5 was reacted according to the same procedure as Example 2 to give the title compound.

$^1$H NMR (CDCl$_3$-d4) δ 0.90 (m, 2H), 1.05 (m, 2H), 1.20 (m, 18H), 3.96 (d, 2H), 4.22 (s, 2H), 5.65 (m, 4H), 8.03 (s, 1H), 8.69 (s, 1H)

ESI: 528 (M+1)$^+$, C22H34N5O8P

Example 7

Synthesis of ({1-[(2-amino-6-cyclopropylamino-9H-purin-9-yl)methyl]cyclopropyl}oxy)methylphosphonic acid (Compound 11)

The compound prepared in Preparation 6 (200 mg) was dissolved in 20 ml of ethanol, 53 ml of triethylamine and 82 mg of cyclopropylamine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 178 mg (Yield 85%) of the diisopropyl compound.

$^1$H NMR (CDCl$_3$) δ 0.59 (t, 2H), 0.83 (m, 4H), 1.00 (t, 2H), 1.24 (d, 6H), 1.29 (d, 6H), 3.0 (brs, 1H), 3.80 (d, 2H), 4.15 (s, 2H), 4.70 (m, 2H), 4.71 (brs, 2H), 5.71 (s, 1H), 7.68 (s, 1H)

The compound thus obtained was treated with trimethylsilylbromide according to the same procedure as Example 1 to give 128 mg (Yield 90%) of the title compound.

$^1$H NMR (MeOH-d4) δ 0.86 (m, 2H), 0.94 (m, 2H), 1.02 (m, 2H), 1.07 (m, 2H), 2.90 (br s, 1H), 3.93 (d, 2H), 4.39 (s, 2H), 8.43 (br s, 1H)

ESI: 355 (M+1)$^+$, C13H19N6O4P

Example 8

Synthesis of ({1-[(2-amino-6-ethylamino-9H-purin-9-yl)methyl]cyclopropyl}oxy)methylphosphonic acid (Compound 13)

The compound prepared in Preparation 6 (115 mg) was dissolved in 2 ml of ethanol, 31 ml of triethylamine and 0.07 ml of ethylamine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 104 mg (Yield 89%) of the diisopropyl compound.

$^1$H NMR (CDCl$_3$) δ 0.82 (m, 2H), 1.00 (m, 2H), 1.24 (d, 6H), 1.27 (t, 3H), 1.29 (d, 6H), 3.60 (brs, 2H), 3.81 (d, 2H), 4.15 (s, 2H), 4.65 (m, 4H), 5.50 (br s, 1H), 7.78 (s, 1H)

The compound thus obtained was reacted according to the same procedure as Example 1 to give 75 mg (Yield 90%) of the title compound.

$^1$H NMR (MeOH-d4) δ 0.89 (m, 2H), 1.04 (m, 2H), 1.31 (t, 3H), 3.59 (br s, 2H), 3.92 (d, 2H), 4.35 (s, 2H), 9.95 (br s, 1H)

ESI: 343 (M+1)$^+$, C13H19N6O4P

Example 9

Synthesis of [(1-{[2-amino-6-(dimethylamino)-9H-purin-9-yl]methyl}cyclopropyl)oxy]methylphosphonic acid (Compound 15)

The compound prepared in Preparation 6 (115 mg) was dissolved in 20 ml of ethanol, 38.6 ml of triethylamine and 1.74 ml of N,N-dimethylamine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 119 mg (Yield 81%) of the diisopropyl compound.

$^1$H NMR (CDCl$_3$) δ 0.75 (t, 2H), 0.93 (t, 2H), 1.16 (d, 6H), 1.22 (d, 6H), 3.3 (brs, 6H), 3.74 (d, 2H), 4.09 (s, 2H), 4.60 (m, 2H), 4.69 (brs, 2H), 7.68 (s, 1H)

The compound thus obtained was reacted according to the same procedure as Example 1 to give 86 mg (Yield 90%) of the title compound.

$^1$H NMR (MeOH-d4) δ 0.89 (m, 2H), 1.05 (m, 2H), 3.30 (br s, 6H), 3.90 (d, 2H), 4.37 (s, 2H), 7.92 (br s, 1H)

ESI: 343 (M+1)$^+$, C12H19N6O4P

Example 10

Synthesis of [(1-{[2-amino-6-(isopropylamino)-9H-purin-9-yl]methyl}cyclopropyl)oxy]methylphosphonic acid (Compound 17)

The compound prepared in Preparation 6 (133 mg) was dissolved in 20 ml of ethanol, 0.049 ml of triethylamine and 0.082 ml of isopropylamine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 95 mg (Yield 68%) of the diisopropyl compound.

$^1$H NMR (CDCl$_3$) δ 0.83 (m, 2H), 0.98 (m, 2H), 1.28 (m, 18H), 3.79 (d, 2H), 4.15 (s, 2H), 4.60 (br s, 1H), 4.68 (s, 2H), 4.70 (m, 2H), 5.40 (br s, 1H), 7.77 (s, 1H)

The compound thus obtained was reacted according to the same procedure as Example 1 to give 72 mg (Yield 91%) of the title compound.

$^1$H NMR (MeOH-d4) δ 0.89 (m, 2H), 1.05 (m, 2H), 1.34 (d, 6H), 3.30 (br s, 1H), 3.90 (d, 2H), 4.36 (s, 2H), 8.01 (br s, 1H)

ESI: 357 (M+1)$^+$, C12H19N6O4P

Example 11

Synthesis of ({1-[(2,6-diamino-9H-purin-9-yl)methyl]cyclopropyl}oxy)methylphosphonic acid (Compound 19)

The compound prepared in Preparation 4 (246 mg) and 2,6-diaminopurine were reacted according to the same procedure as Preparation 5 to give 78.5 mg (Yield 29%) of the diisopropyl compound.

$^1$H NMR (CDCl$_3$) δ 0.85 (t, 2H), 1.00 (t, 2H), 1.25 (d, 6H), 1.29 (d, 6H), 1.83 (brs, 2H), 3.82 (d, 2H), 4.15 (s, 2H), 4.68 (m, 2H), 5.39 (d, 2H), 7.85 (s, 1H)

ESI: 399 (M+1)$^+$, C16H27N6O4P

The compound thus obtained was reacted according to the same procedure as Example 1 to give 72 mg (Yield 91%) of the title compound.

$^1$H NMR (DMSO-d6+CF$_3$COOH) δ 0.70 (m, 2H), 0.82 (m, 2H), 3.58 (d, 2H), 4.21 (s, 2H), 8.16 (br s, 1H)

ESI: 315 (M+1)$^+$, C10H15N6O4P

Example 12

Synthesis of ({1-[(2-amino-6-ethoxy-9H-purin-9-yl)methyl]cyclopropyl}oxy)methylphosphonic acid (Compound 23)

6-Chloroguanine derivative prepared in Preparation 6 (100 mg) was dissolved in 10 ml of ethanol, 32 ml of triethylamine and 53 mg of sodium methoxide were added, and the resulting mixture was refluxed for 4 hours. The reaction was stopped by adding 10 ml of water. The reaction solution was extracted with dichloromethane and distilled under reduced pressure. The residue was purified by silica gel column to give a compound wherein 6-position of guanine was substituted by ethoxy group.

$^1$H NMR (CDCl$_3$) δ 0.83 (t, 2H), 1.00 (t, 2H), 1.24-1.28 (m, 12H), 1.45 (t, 3H), 3.82 (d, 2H), 4.21 (s, 2H), 4.53 (m, 2H), 4.67 (m, 1H), 5.76 (s, 2H), 7.90 (s, 1H)

The compound thus obtained was reacted according to the same procedure as Example 1 to give the title compound.

$^1$H NMR (MeOH-d4) δ 0.99 (t, 2H), 1.06 (t, 2H), 1.48 (t, 3H), 3.91 (d, 2H), 4.51 (s, 2H), 4.65 (m, 2H), 9.18 (s, 1H)

ESI: 344 (M+1)$^+$, C12H18N5O5P

Example 13

Synthesis of ({1-[(2-amino-6-methyl-9H-purin-9-yl)methyl]cyclopropyl}oxy)methylphosphonic acid (Compound 25)

10 ml flask was dried under vacuum and 53 mg (0.238 mmol) of zinc bromide was introduced bit by bit under nitrogen atmosphere. 2 ml of dry tetrahydrofuran was added dropwise thereto, the temperature was lowered to −78° C., 0.08 ml (20.238 mmol) of methylmagnesium bromide was added, and the resulting mixture was stirred for 1 hour. After the reaction mixture was warmed to room temperature, about 10 mol % of palladiumtetrakistriphenylphosphine was added bit by bit. 50 mg (0.119 mmol) of the compound prepared in Preparation 6 in 1 ml of tetrahydrofuran was added to the above reaction solution dropwise. The resulting mixture was heated for 1 hour. The solvent was removed by distillation under reduced pressure, the residue was participated with water and ethyl acetate, and the organic layer was concentrated by distillation under reduced pressure. The residue was purified by silica gel column chromatography (eluent: methylene chloride/methanol=90/10, v/v) to give 20 mg (Yield 42%) of the diisopropyl compound.

$^1$H NMR (MeOH-d4) δ 0.95 (m, 2H), 0.98 (m, 2H), 1.17 (d, 6H), 1.23 (d, 6H), 2.59 (s, 3H), 4.02 (s, 1H), 4.10 (s, 1H), 4.32 (s, 2H), 4.59 (m, 2H), 8.12 (s, 1H)

ESI: 398 (M+1)$^+$, C17H28N5O4P

The compound thus obtained was reacted according to the same procedure as Example 1 to give 8.0 mg (Yield 50%) of the title compound.

$^1$H NMR (D$_2$O) δ 0.87 (m, 2H), 1.02 (m, 2H), 3.79 (s, 1H), 3.81 (s, 1H), 4.53 (s, 2H), 8.25 (s, 1H)

ESI: 314 (M+1)$^+$, C11H16N5O4P

Example 14

Synthesis of [(1{[5-methyl-2,4-dioxo-3,4-dihydro-1 (2H)-pyrimidinyl]methyl}cyclopropyl)oxy]methylphosphonic acid (Compound 31)

The compound prepared in Preparation 7 (19 mg) was reacted according to the same procedure as Example 1 to give 14 mg (Yield 95%) of the title compound.

ESI: 291 (M+1)$^+$, C10H11N2O6P $^1$H NMR (MeOH-d4) δ 0.82 (t, 2H), 0.97 (t, 2H), 1.87 (s, 3H), 3.83 (d, 2H), 3.97 (s, 2H), 7.55 (s, 1H)

Example 15

Synthesis of [(1-{[2-amino-6-(4-morpholinyl)-9H-purin-9-yl]methyl}cyclopropyl)oxy]methylphosphonic acid (Compound 37)

The compound prepared in Preparation 6 (134 mg) was dissolved in 20 ml of ethanol, 0.049 ml of triethylamine and 0.085 ml of morpholine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 66 mg (Yield 44%) of the diisopropyl compound.

$^1$H NMR (CDCl$_3$) δ 0.83 (m, 2H), 0.99 (m, 2H), 1.24 (d, 6H), 1.30 (d, 6H), 3.79 (m, 6H), 4.18 (s, 2H), 4.21 (br s, 4H), 4.67 (m, 2H), 4.80 (br s, 2H), 7.78 (s, 1H)

ESI: 469 (M+1)$^+$, C20H33N6O5P

The compound thus obtained was treated with trimethylsilylbromide according to the same procedure as Example 1 to give 49 mg (Yield 91%) of the title compound.

$^1$H NMR (MeOH-d4) δ 0.89 (m, 2H), 1.07 (m, 2H), 3.81 (m, 4H), 3.92 (d, 2H), 4.40 (br s, 6H), 7.87 (s, 1H)

ESI: 384 (M+1)$^+$, C14H21N6O5P

Example 16

Synthesis of [(1-{[2-amino-6-(1-piperidinyl)-9H-purin-9-yl]methyl}cyclopropyl)oxy]methylphosphonic acid (Compound 39)

The compound prepared in Preparation 6 (154 mg) was dissolved in 20 ml of ethanol, 0.049 ml of triethylamine and 0.11 ml of piperidine were added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 123 mg (Yield 72%) of the diisopropyl compound.

$^1$H NMR (CDCl$_3$) δ 0.80 (m, 2H), 0.99 (m, 2H), 1.22 (d, 6H), 1.26 (d, 6H), 1.63 (m, 4H), 1.67 (m, 2H), 3.78 (d, 2H), 4.14 (s, 6H), 4.54 (br s, 2H), 4.65 (m, 2H), 7.72 (s, 1H) ESI: 467 (M+1)$^+$, C21H35N6O4P

The compound thus obtained was reacted according to the same procedure as Example 1 to give 87 mg (Yield 91%) of the title compound.

$^1$H NMR (MeOH-d4) δ 0.89 (m, 2H), 1.06 (m, 2H), 1.73 (m, 4H), 1.79 (m, 2H), 3.90 (d, 2H), 4.37 (s, 2H), 4.43 (br s, 4H), 7.89 (s, 1H)

ESI: 383 (M+1)$^+$, C15H23N6O4P

Example 17

Synthesis of [(1-{[2-amino-6-(4-methyl-1-piperazinyl)-9H-purin-9-yl]methyl}cyclopropyl)oxy]methylphosphonic acid (Compound 41)

The compound prepared in Preparation 6 (128 mg) was dissolved in 20 ml of ethanol, 0.10 ml of 4-methyl-1-piperazine was added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 123 mg (Yield 83%) of the diisopropyl compound.

$^1$H NMR (CDCl$_3$) δ 0.80 (m, 2H), 0.98 (m, 2H), 1.21 (d, 6H), 1.27 (d, 6H), 2.30 (s, 3H), 2.48 (m, 4H), 3.78 (d, 2H), 4.13 (s, 2H), 4.22 (br s, 4H), 4.57 (s, 2H), 4.66 (m, 2H), 7.73 (s, 1H)

ESI: 482 (M+1)$^+$, C21H36N7O4P

The compound thus obtained was reacted according to the same procedure as Example 1 to give 87 mg (Yield 85%) of the title compound.

$^1$H NMR (MeOH-d4) δ 0.89 (m, 2H), 1.07 (m, 2H), 3.00 (s, 3H), 3.72 (m, 4H), 3.91 (d, 2H), 4.45 (s, 2H), 4.89 (m, 2H), 5.70 (br, 2H), 7.91 (s, 1H)

ESI: 398 (M+1)$^+$, C15H24N7O4P

Example 18

Synthesis of [(1-{[2-amino-6-(1-pyrrolidinyl)-9H-purin-9-yl]methyl}cyclopropyl)oxy]methyl phosphonic acid (Compound 43)

The compound prepared in Preparation 6 (122 mg) was dissolved in 20 ml of ethanol, 0.07 ml of pyrrolidine was added thereto, and the resulting mixture was heated under reflux for 18 hours. Water was added to stop the reaction, and the product was extracted with ethyl acetate. The ethyl acetate extract was concentrated by distillation under reduced pressure and the residue was purified by silica gel column chromatography (eluent: dichloromethane/methanol=20/1, v/v) to give 110 mg (Yield 83%) of the diisopropyl compound.

$^1$H NMR (CDCl$_3$) δ 0.78 (m, 2H), 0.96 (m, 2H), 1.20 (d, 6H), 1.26 (d, 6H), 2.00 (br s, 4H), 3.60 (br, 3H), 3.78 (d, 2H), 4.09 (br, 2H), 4.12 (s, 2H), 4.63 (m, 2H), 7.69 (s, 1H)

ESI: 453 (M+1)$^+$, C20H33N6O4P

The compound thus obtained was reacted according to the same procedure as Example 1 to give 76 mg (Yield 85%) of the title compound.

¹H NMR (MeOH-d4) δ 0.94 (m, 2H), 1.03 (m, 2H), 2.15 (m, 4H), 3.76 (m, 2H), 3.91 (d, 2H), 4.18 (m, 2H), 4.40 (s, 2H), 5.70 (br, 2H), 8.42 (s, 1H)
ESI: 369 (M+1)$^+$, C14H21N6O4P

Example 19

Synthesis of 3-[({1-[(2-amino-9H-purin-9-yl)methyl]cyclopropyl}oxy)methyl]-9-methyl-3,7-dioxo-2,4,6-trioxa-38$^5$-phosphadec-1-yl 3-methylbutanoate (Compound 74)

The compound prepared in Example 5 (100 mg) was dissolved in dimethylformamide (2 ml) and then reacted with chloromethyl 3-methylbutyrate in the presence of triethylamine (3 equivalents) at room temperature for 24 hours. The resulting product was purified by silica gel column to give the title compound in a yield of 41%.

¹H NMR (CDCl₃) δ 0.89 (t, 2H), 0.94 (d, 12H), 1.04 (t, 2H), 2.10 (m, 2H), 2.22 (d, 4H), 3.97 (d, 2H), 4.23 (s, 2H), 5.21 (s, 2H), 5.65 (m, 4H), 8.00 (s, 1H), 8.69 (s, 1H)
ESI: 527 (M+1)$^+$, C23H35N4O8P

Example 20

Synthesis of 3-[({1-[(2-amino-9H-purin-9-yl)methyl]cyclopropyl}oxy)methyl]-3,7-dioxo-2,4,6-trioxa-38$^5$-phosphadec-1-yl butyrate (Compound 75)

The compound prepared in Example 5 was reacted with chloromethyl butyrate according to the same procedure as Example 19 at room temperature for 24 hours. The resulting product was purified by silica gel column to give the title compound in a yield of 24%.

¹H NMR (CDCl₃) δ 0.88 (t, 2H), 0.92 (d, 6H), 1.60 (m, 4H), 2.32 (t, 4H), 3.96 (d, 2H), 4.22 (s, 2H), 5.00 (s, 2H), 5.62 (m, 4H), 8.00 (s, 1H), 8.68 (s, 1H)
ESI: 499 (M+1)$^+$, C21H31N4O8P

Example 21

Synthesis of 3-[({1-[(2-amino-9H-purin-9-yl)methyl]cyclopropyl}oxy)methyl]-8-methyl-3,7-dioxo-2,4,6-trioxa-38$^5$-phosphanon-1-yl 2-methylpropanoate (Compound 78)

The compound prepared in Example 5 was reacted with chloromethyl isobutyrate according to the same procedure as Example 19 at room temperature for 24 hours. The resulting product was purified by silica gel column to give the title compound in a yield of 21%.

¹H NMR (CDCl₃) δ 0.84 (t, 2H), 0.97 (t, 2H), 1.11 (d, 12H), 2.52 (m, 2H), 3.91 (d, 2H), 4.16 (s, 2H), 5.21 (s, 2H), 5.58 (m, 4H), 7.96 (s, 1H), 8.61 (s, 1H)
ESI: 499 (M+1)$^+$, C21H31N4O8P

Example 22

Synthesis of 3-[({1-[(2-amino-9H-purin-9-yl)methyl]cyclopropyl}oxy)methyl]-3,7-dioxo-7-(1-pyrrolidinyl)-2,4,6-trioxa-38$^5$-phosphahept-1-yl-pyrrolidinecarboxylate (Compound 80)

The compound prepared in Example 5 was reacted with chloromethyl 1-pyrrolidinecarboxylate according to the same procedure as Example 19 at room temperature for 24 hours. The resulting product was purified by silica gel column to give the title compound in a yield of 35%.

¹H NMR (CDCl₃) δ 0.82 (t, 2H), 0.87 (m, 8H), 0.98 (t, 2H), 1.57 (d, 4H), 2.26 (t, 4H), 3.91 (d, 2H), 4.16 (s, 2H), 5.12 (s, 2H), 5.57 (m, 4H), 7.98 (s, 1H), 8.62 (s, 1H)
ESI: 553 (M+1)$^+$, C23H33N6O8P

Example 23

Synthesis of 3-[({1-[(2-amino-9H-purin-9-yl)methyl]cyclopropyl}oxy)methyl]-3,7-dioxo-7-(1-piperidinyl)-2,4,6-trioxa-38$^5$-phosphahept-1-yl 1-piperidinecarboxylate (Compound 81);

The compound prepared in Example 5 was reacted with chloromethyl 1-piperidinecarboxylate according to the same procedure as Example 19 at room temperature for 24 hours. The resulting product was purified by silica gel column to give the title compound in a yield of 39%.

¹H NMR (CDCl₃) δ 0.86 (t, 2H), 1.02 (t, 2H), 1.47-1.58 (brm, 12H), 3.40 (brm, 8H), 3.99 (d, 2H), 4.22 (s, 2H), 5.00 (s, 2H), 5.69 (m, 4H), 8.00 (s, 1H), 8.67 (s, 1H)
ESI: 581 (M+1)$^+$, C25H37N6O8P

Example 24

Synthesis of 3-[({1-[(2-amino-9H-purin-9-yl)methyl]cyclopropyl}oxy)methyl]-7-(4-morpholinyl)-3,7-dioxo-2,4,6-trioxa-38$^5$-phosphahept-1-yl 4-morpholinecarboxylate (Compound 82)

The compound prepared in Example 5 was reacted with chloromethyl 4-morpholinecarboxylate according to the same procedure as Example 19 at room temperature for 24 hours. The resulting product was purified by silica gel column to give the title compound in a yield of 40%.

¹H NMR (CDCl₃) δ 0.89 (t, 2H), 1.03 (t, 2H), 3.47 (brm, 8H), 3.65 (brm, 8H), 4.00 (d, 2H), 4.24 (s, 2H), 5.04 (s, 2H), 5.70 (m, 4H), 8.07 (s, 1H), 8.69 (s, 1H)
ESI: 586 (M+1)$^+$, C23H33N6O10P

Example 25

Synthesis of {[1-({2-amino-6-[(4-methylphenyl)sulfanyl]-9H-purin-9-yl}methyl)cyclopropyl]oxy}methylphosphonic acid (Compound 66)

6-Chloroguanine derivative prepared in Preparation 6 (4.86 g) was dissolved in 85 ml of methanol and 1.4 g of triethylamine and 2.9 g of 4-methylthiocresol were added. The reaction mixture was reacted under reflux condition for 24 hours. The reaction was stopped by adding 20 ml of water, and the methanol was removed by distillation under reduced pressure. The reaction mixture was extracted with dichloromethane and purified by silica gel column to give a compound wherein 6-position of guanine was substituted by 4-methylphenylthio group.

¹H NMR (CDCl₃) δ 0.84 (t, 2H), 1.02 (t, 2H), 1.25-1.31 (m, 12H), 2.40 (s, 3H), 4.20 (d, 2H), 4.69 (m, 2H), 4.74 (s, 2H), 7.22 (d, 2H), 7.50 (d, 2H), 8.00 (s, 1H)

The compound thus obtained was reacted according to the same procedure as Example 1 and then recrystallized from a mixture of methanol-diethylether (1/20, v/v) to give the title compound.

¹H NMR (MeOH-d4) δ 0.98 (t, 2H), 1.06 (t, 2H), 2.42 (s, 3H), 3.92 (d, 2H), 4.48 (s, 2H), 7.35 (d, 2H), 7.55 (d, 2H), 9.05 (s, 1H)
ESI: 421 (M+1)$^+$, C18H21N4O4PS

Example 26

Synthesis of 3-({[1-({2-amino-6-[(4-methylphenyl)sulfanyl]-9H-purin-9-yl}methyl)cyclopropyl]oxy}methyl)-8,8-dimethyl-3,7-dioxo-2,4,6-trioxa-3$^5$-phosphanon-1-yl pivalate (Compound 68)

The methylphosphonic acid prepared in Example 25 was reacted according to the same procedure as Example 2 to give the title compound.

$^1$H NMR (CDCl$_3$) δ 0.82 (t, 2H), 0.98 (t, 2H), 1.18 (s, 18H), 2.36 (s, 3H), 3.93 (d, 2H), 4.15 (s, 2H), 4.93 (s, 2H), 5.60 (m, 4H), 7.18 (d, 2H), 7.48 (d, 2H), 7.88 (s, 1H)

ESI: 649 (M+1)$^+$, C30H41N4O8PS

Example 27

Synthesis of {[1-({2-amino-6-[(4-methoxyphenyl)sulfanyl]-9H-purin-9-yl}methyl)cyclopropyl]oxy}methylphosphonic acid (Compound 96)

6-Chloroguanine derivative prepared in Preparation 6 (4.86 g) was dissolved in 85 ml of methanol and 1.4 g of triethylamine and 2.9 g of 4-methoxythiocresol were added. The reaction mixture was reacted under reflux condition for 24 hours. The reaction was stopped by adding 20 ml of water, and the methanol was removed by distillation under reduced pressure. The reaction mixture was extracted with dichloromethane and purified by silica gel column to give a compound wherein 6-position of guanine was substituted by 4-methoxyphenylthio group.

The compound thus obtained was reacted according to the same procedure as Example 1 and then recrystallized from a mixture of methanol-diethylether (1/20, v/v) to give the title compound.

$^1$H NMR (MeOH-d4) δ 0.77 (m, 2H), 1.05 (m, 2H), 3.87 (s, 3H), 3.92 (d, 2H), 4.45 (s, 2H), 7.10 (d, 2H), 7.59 (d, 2H), 8.09 (s, 1H)

ESI: 438 (M+1)$^+$, C17H20N5O5PS

Example 28

Synthesis of {[1-({2-amino-6-[(4-nitrophenyl)sulfanyl]-9H-purin-9-yl}methyl)cyclopropyl]oxy}methylphosphonic acid (Compound 95)

The compound prepared in Preparation 6 was reacted according to the same procedure as Example 27 except that 4-nitrothiocresol was used instead of 4-methoxythiocresol to give the title compound.

$^1$H NMR (MeOH-d4) δ 0.86 (m, 2H), 0.95 (m, 2H), 3.82 (d, 2H), 4.35 (s, 2H), 7.81 (d, 2H), 8.22 (d, 2H), 8.72 (s, 1H)

ESI: 453 (M+1)$^+$, C16H17N6O6PS

Example 29

Synthesis of ({1-[(2-amino-6-hydroxy-9H-purin-9-yl)methyl]-2-methylcyclopropyl}oxy)methylphosphonic acid (Compound 97)

The 6-chloroguanine derivative prepared in Preparation 12 was consecutively reacted according to the same procedure as Examples 3 and 4 to give the title compound.

$^1$H NMR (MeOH-d4) δ 0.73 (t, 1H), 1.15 (m, 1H), 1.21 (d, 3H), 1.38 (t, 1H), 1.48 (m, 1H), 3.85 (t, 1H), 3.96 (t, 1H), 4.42 (d, 1H), 4.69 (d, 1H), 9.12 (s, 1H)

Example 30

Synthesis of {[1-({2-amino-[6-(4-methoxyphenyl)sulfanyl]-9H-purin-9-yl}methyl)-2-methylcyclopropyl]oxy}methylphosphonic acid (Compound 99)

The 6-chloroguanine derivative prepared in Preparation 12 was reacted according to the same procedure as Example 27 to give the title compound.

$^1$H NMR (MeOH-d4) δ 0.67 (t, 1H), 1.13 (m, 2H), 1.20 (d, 3H), 1.45 (m, 1H), 3.85 (m, 1H), 3.86 (s, 3H), 3.94 (m, 1H), 4.42 (d, 1H), 4.68 (d, 1H), 7.09 (d, 2H), 7.59 (d, 2H), 9.00 (s, 1H)

ESI: 452 (M+1)$^+$, C18H22N5O5PS

Example 31

Synthesis of {[1-({2-amino-[6-(4-methylphenyl)sulfanyl]-9H-purin-9-yl}methyl)-2-methylcyclopropyl]oxy}methylphosphonic acid (Compound 101)

The 6-chloroguanine derivative prepared in Preparation 12 was reacted according to the same procedure as Example 25 to give the title compound.

$^1$H NMR (MeOH-d4) δ 0.68 (t, 1H), 1.15 (m, 2H), 1.20 (d, 3H), 1.45 (m, 1H), 2.42 (s, 3H), 3.84 (m, 1H), 3.96 (m, 1H), 4.43 (d, 1H), 4.68 (d, 1H), 7.36 (d, 2H), 7.55 (d, 2H), 9.05 (s, 1H)

ESI: 436 (M+1)$^+$, C18H22N5O4PS

Example 32

Synthesis of {[1-({2-amino-[6-(4-nitrophenyl)sulfanyl]-9H-purin-9-yl}methyl)-2-methylcyclopropyl]oxy}methylphosphonic acid (Compound 100)

The 6-chloroguanine derivative prepared in Preparation 12 was reacted according to the same procedure as Example 28 to give the title compound.

$^1$H NMR (MeOH-d4) δ 0.49 (t, 1H), 0.93 (m, 1H), 1.00 (d, 3H), 1.25 (m, 1H), 3.64 (m, 1H), 3.76 (m, 1H), 4.28 (d, 1H), 4.53 (d, 1H), 7.72 (d, 2H), 8.14 (d, 2H), 9.10 (s, 1H)

ESI: 467 (M+1)$^+$, C17H19N6O6PS

Example 33

Synthesis of ({1-[(6-amino-9H-purin-9-yl)methyl]-2-methylcyclopropyl}oxy)methylphosphonic acid (Compound 103)

The adenine derivative prepared in Preparation 11 was reacted according to the same procedure as Example 1 to give the title compound.

$^1$H NMR (MeOH-d4) δ 0.64 (t, 1H), 1.09 (m, 1H), 1.20 (d, 3H), 1.43 (m, 1H), 3.83 (m, 1H), 3.95 (m, 1H), 4.49 (d, 1H), 4.75 (d, 1H), 5.49 (s, 2H), 8.39 (s, 1H), 8.55 (s, 1H)

ESI: 314 (M+1)$^+$, C11H16N5O4P

Example 34

Synthesis of bis{[(t-butoxycarbonyl)oxy]methyl} ({1-[(2-amino-9H-purin-9-yl)methyl]cyclopropyl}oxy)methylphosphonate (Compound 69)

The compound prepared in Example 5 (187 mg) was mixed with 6 ml of N-methyl-2-pyrrolidone, and 300 mg of triethylamine and 150 mg of chloromethyl t-butylcarbonate were added. The reaction solution was stirred at room temperature for 4 hours. The reaction was stopped by adding 10 ml of water, and the reaction mixture was extracted with ethyl acetate. The extract was distilled under reduced pressure and purified by silica gel column to give the title compound.

$^1$H NMR (CDCl$_3$) δ 0.86 (m, 2H), 1.06 (m, 2H), 1.47 (s, 18H), 4.01 (d, 4H), 4.22 (s, 2H), 5.00 (brs, 2H), 5.61 (m, 4H), 7.99 (s, 1H), 8.69 (s, 1H)

ESI: 344 (M+1)$^+$, C22H34N5O10P

Example 35

Synthesis of bis{[(isopropoxycarbonyl)oxy]methyl} ({1-[(2-amino-9H-purin-9-yl)methyl] cyclopropyl}oxy)methylphosphonate (Compound 70)

The compound prepared in Example 5 (100 mg) was mixed with 5 ml of N-methyl-2-pyrrolidone, and 110 mg of triethylamine and 150 mg of chloromethyl isopropylcarbonate were added. The reaction solution was stirred at 50 for 4 hours. The reaction was stopped by adding 10 ml of water, and the reaction mixture was extracted with ethyl acetate. The extract was distilled under reduced pressure and purified by silica gel column to give the title compound.

$^1$H NMR (CDCl$_3$) δ 0.88 (s, 2H), 1.06 (s, 2H), 1.29 (d, 2H), 1.31 (d, 2H), 4.01 (d, 4H), 4.21 (s, 2H), 4.92 (m, 2H), 5.01 (brs, 2H), 5.64 (m, 4H), 7.99 (s, 1H), 8.69 (s, 1H)

ESI: 532 (M+1)$^+$, C20H30N5O10P

Example 36

Synthesis of ({1-[(2-amino-6-hydroxy-9H-purin-9-yl)methyl]-2,2-dimethyl cyclopropyl}oxy)methylphosphonic acid (Compound 146)

The compound prepared in Preparation 32 was consecutively reacted according to the same procedure as Examples 1 and 4 to give the title compound.

$^1$H NMR (MeOH-d4) δ 0.78 (d, 1H), 0.82 (d, 1H), 1.21 (s, 3H), 1.27 (s, 3H), 3.90 (d, 1H), 3.91 (d, 1H), 4.58 (s, 2H), 9.12 (s, 1H)

ESI: 344 (M+1)$^+$, C12H18N5O5P

Example 37

Synthesis of ({1-[(2-amino-9H-purin-9-yl)methyl]-2,2-dimethylcyclopropyl}oxy)methylphosphonic acid (Compound 147)

The compound prepared in Preparation 32 was reacted according to the same procedure as Example 5 to give a compound wherein 6-position of guanine was reduced by hydrogen.

$^1$H NMR (CDCl$_3$) δ 0.60 (d, 1H), 0.82 (d, 1H), 1.21 (s, 3H), 1.22 (s, 3H), 1.22 (m, 15H), 3.73 (m, 1H), 3.87 (m, 1H), 4.13 (d, 1H), 4.49 (d, 1H), 4.67 (m, 2H), 4.98 (brs, 2H), 8.09 (s, 1H), 9.67 (s, 1H)

The compound thus obtained was reacted according to the same procedure as Example 1 to give the title compound.

$^1$H NMR (MeOH-d4) δ 0.74 (d, 1H), 0.81 (d, 1H), 1.21 (s, 3H), 1.26 (s, 3H), 3.91 (d, 2H), 4.49 (d, 1H), 4.57 (d, 1H), 8.63 (s, 1H), 8.74 (s, 1H)

ESI: 328 (M+1)$^+$, C12H18N5O4P

Example 38

Synthesis of ({1-[(6-amino-9H-purin-9-yl)methyl]-2,2-dimethylcyclopropyl}oxy)methylphosphonic acid (Compound 148)

The compound prepared in Preparation 31 was reacted according to the same procedure as Example 1 to give the title compound.

$^1$H NMR (MeOH-d4) δ 0.77 (d, 1H), 0.79 (d, 1H), 1.25 (s, 3H), 1.28 (s, 3H), 3.90 (d, 2H), 4.61 (d, 1H), 4.70 (d, 1H), 8.38 (s, 1H), 8.51 (s, 1H)

ESI: 328 (M+1)$^+$, C12H18N5O4P

Example 39

Synthesis of (E)-2-{1-[(2-amino-6-hydroxy-9H-purin-9-yl)methyl]cyclopropyl}ethenylphosphonic acid (Compound 130)

The compound prepared in Preparation 26 was reacted according to the same procedure as Example 1 to give phosphonic acid derivative.

$^1$H NMR (MeOH-d4) δ 1.07 (t, 2H), 1.33 (t, 1H), 4.41 (s, 2H), 5.76 (dd, 1H), 6.45 (dd, 1H), 9.18 (s, 1H)

The compound thus obtained was reacted according to the same procedure as Example 4 to give the title compound.

$^1$H NMR (MeOH-d4) δ 1.08 (t, 2H), 1.34 (t, 1H), 4.38 (s, 2H), 5.78 (dd, 1H), 6.46 (dd, 1H), 9.11 (s, 1H)

ESI: 312 (M+1)$^+$, C11H14N5O4P

Example 40

Synthesis of 2-{1-[(2-amino-9H-purin-9-yl)methyl] cyclopropyl}ethyl phosphonic acid (Compound 139)

The compound prepared in Preparation 26 was reacted according to the same procedure as Example 5 to give the title compound.

$^1$H NMR (MeOH-d4) δ 0.58 (t, 2H), 0.85 (t, 2H), 1.42 (m, 2H), 1.95 (m, 2H), 4.11 (s, 2H), 5.78 (dd, 1H), 8.55 (s, 1H), 8.75 (s, 1H)

ESI: 298 (M+1)$^+$, C11H16N5O3P

Example 41

Synthesis of (E)-2-{1-[(6-amino-9H-purin-9-yl)methyl]cyclopropyl}ethenyl phosphonic acid (Compound 132)

The compound prepared in Preparation 25 was reacted according to the same procedure as Example 1 to give the title compound.

$^1$H NMR (MeOH-d4) δ 0.94 (t, 2H), 1.20 (t, 2H), 4.36 (s, 2H), 5.63 (dd, 1H), 6.37 (dd, 1H), 8.30 (s, 1H), 8.31 (s, 1H)

ESI: 296 (M+1)$^+$, C11H14N5O3P

Example 42

Synthesis of 2-{1-[(6-amino-9H-purin-9-yl)methyl] cyclopropyl}ethyl phosphonic acid (Compound 140)

The compound prepared in Preparation 25 was reacted according to the same procedure as Example 5 to give the title compound.

$^1$H NMR (MeOH-d4) δ 0.58 (t, 2H), 0.87 (t, 2H), 1.37 (m, 2H), 1.97 (m, 2H), 4.24 (s, 2H), 8.31 (s, 1H), 8.42 (s, 1H)

ESI: 298 (M+1)$^+$, C11H16N5O3P

Example 43

Synthesis of 2-{1-[(2-amino-6-hydroxy-9H-purin-9-yl)methyl]cyclopropyl}ethylphosphonic acid (Compound 138)

The compound prepared in Preparation 26 was reacted according to the same procedure as Example 12 to give a compound wherein 6-position of guanine was substituted by ethoxy group.

$^1$H NMR (CDCl$_3$) δ 1.00 (t, 2H), 1.10 (t, 2H), 1.16-1.21 (m, 9H), 3.90 (m, 4H), 4.01 (m, 2H), 4.13 (s, 2H), 4.92 (s, 2H), 5.58 (dd, 1H), 6.49 (dd, 1H), 7.62 (s, 1H)

The compound thus obtained (80 mg) was dissolved in methanol and reacted under hydrogen atrmosphere in the presence of 20 mg of 10% Pd/C to give a compound wherein double bond was reduced.

$^1$H NMR (CDCl$_3$) δ 0.49 (t, 2H), 0.66 (t, 2H), 1.21 (t, 6H), 1.42 (m, 2H), 2.01 (m, 2H), 3.99 (m, 6H), 4.96 (s, 2H), 7.59 (s, 1H)

The compound thus obtained was reacted according to the same procedure as Example 1 to give the title compound.

$^1$H NMR (MeOH-d4) δ 0.60 (t, 2H), 0.87 (t, 2H), 1.47 (m, 2H), 1.97 (m, 2H), 4.16 (s, 2H), 9.12 (s, 1H)

ESI: 314 (M+1)$^+$, C11H16N5O4P

Example 44

Synthesis of 2-{1-[(2-amino-9H-purin-9-yl)methyl]cyclopropyl}propyl phosphonic acid (Compound 144)

The compound prepared in Preparation 35 was consecutively reacted according to the same procedure as Preparations 24, 26 and Example 5 to give the title compound.

$^1$H NMR (MeOH-d4) δ 0.62-0.77 (m, 4H), 1.04 (d, 3H), 1.52 (m, 2H), 1.90 (m, 1H), 4.24 (m, 2H), 8.58 (s, 1H), 8.74 (s, 1H)

ESI: 312 (M+1)$^+$, C12H18N5O3P

Example 45

Synthesis of (E)-2-{1-[(6-amino-9H-purin-9-yl)methyl]cyclopropyl}-1-propenylphosphonic acid (Compound 137)

The compound prepared in Preparation 35 was consecutively reacted according to the same procedure as Preparations 24, 25 and Example 1 to give the title compound.

$^1$H NMR (MeOH-d4) δ 0.86 (t, 2H), 1.10 (t, 2H), 2.19 (d, 3H), 4.38 (s, 2H), 5.23 (d, 1H), 8.34 (s, 1H), 8.37 (s, 1H)

ESI: 310 (M+1)$^+$, C12H16N5O3P

Example 46

Synthesis of 2-{1-[(6-amino-9H-purin-9-yl)methyl]cyclopropyl}propyl phosphonic acid (Compound 143)

The compound prepared in Preparation 35 was consecutively reacted according to the same procedure as Preparations 24, 25 and Example 5 to give the title compound.

$^1$H NMR (MeOH-d4) δ 0.65 (t, 2H), 0.78 (t, 2H), 0.95 (m, 1H), 1.00 (d, 3H), 1.53 (s, 1H), 1.90 (m, 1H), 4.3 (q, 2H), 8.41 (s, 1H), 8.45 (s, 1H)

ESI: 312 (M+1)$^+$, C12H18N5O3P

Example 47

Synthesis of bis(2,2,2-trifluoroethyl)({1-[(6-amino-9H-purin-9-yl)methyl]cyclopropyl}oxy)methylphosphonate (Compound 48)

To the methylphosphonic acid prepared in Example 1 (150 mg) was added dropwise dichloromethane, 0.73 ml of N,N-diethyltrimethylsilylamine was added dropwise thereto, and the resulting mixture was stirred at room temperature for 2 hours. Oxalyl chloride (0.15 ml) and 2 drops of dimethylformamide were added to the reaction vessel. The mixture was stirred for further 2 hours and the solvent was removed by distillation under reduced pressure. To the residue were added 10 ml of pyridine and 2 ml of trifluoroethanol, which was then reacted under stirring for 16 hours. The solvent was removed by distillation under reduced pressure and the residue was purified by silica gel column to give the title compound.

$^1$H NMR (CD$_3$OD) δ 1.02 (m, 4H), 4.30 (d, 2H), 4.53 (m, 6H), 8.40 (s, 1H), 8.46 (s, 1H)

ESI: 464 [M+H]+: C14H16F6N5O4P

Example 48

Synthesis of bis(2,2,2-trifluoroethyl)({1-[(2-amino-9H-purin-9-yl)methyl]cyclopropyl}oxy)methylphosphonate (Compound 49)

The compound prepared in Example 5 was reacted according to the same procedure as Example 47 to give the title compound.

$^1$H NMR (CDCl$_3$) δ 0.88 (m, 2H), 1.04 (m, 2H), 4.07 (d, 2H), 4.22 (s, 2H), 4.33 (m, 4H), 5.06 (br.s, 2H), 7.92 (s, 1H), 8.68 (s, 1H)

ESI: 464 [M+H]$^+$, C14H16F6N5O4P

Example 49

Synthesis of bis(2,2,2-trifluoroethyl)[1-({2-amino-[6-(4-methylphenyl)sulfanyl]-9H-purin-9-yl}methyl)cyclopropyl]oxy}methylphosphonate (Compound 62)

The compound prepared in Example 25 was reacted according to the same procedure as Example 47 to give the title compound.

$^1$H NMR (CDCl$_3$) δ 0.88 (m, 2H), 1.03 (m, 2H), 2.39 (s, 3H), 4.06 (d, 2H), 4.19 (s, 2H), 4.33 (m, 4H), 4.76 (br.s, 2H), 7.22 (d, 2H), 7.50 (d, 2H), 7.82 (s, 1H)

ESI: 586 [M+H]+, C21H22F6N5O4PS

Example 50

Synthesis of bis(2,2,2-trifluoroethyl)[(1-{[2-amino-6-hydroxy-9H-purin-9-yl]methyl}cyclopropyl)oxy]methylphosphonate (Compound 45)

The compound prepared in Example 4 was reacted according to the same procedure as Example 47 to give the title compound.

$^1$H NMR (CDCl$_3$) δ 0.91 (m, 2H), 1.05 (m, 2H), 4.08 (d, 2H), 4.17 (s, 2H), 4.35 (m, 4H), 4.70 (s, 2H), 7.69 (s, 1H)

MW=478 [M+H]+479 C14H16F6N5O5P

Example 51

Synthesis of bis(2,2,2-trifluoroethyl)(1-{[2-amino-6-cyclopropylamino-9H-purin-9-yl]methyl}cyclopropyl)oxy]methylphosphonate (Compound 50)

The compound prepared in Example 7 was reacted according to the same procedure as Example 47 to give the title compound.

$^1$H NMR (CDCl$_3$) δ 0.60 (br.s, 2H), 0.84 (br.s, 4H), 1.01 (m, 2H), 2.98 (br.s, 1H), 4.05 (d, 2H), 4.14 (m, 4H), 4.70 (br.s, 2H), 5.67 (br.s, 1H), 7.60 (s, 1H)

ESI: 519, [M+H]+, C17H21F6N6O4P

Example 52

Synthesis of ({1-[(2-amino-9H-purin-9-yl)methyl]-2-methylcyclopropyl}oxy)methylphosphonic acid (Compound 98)

The 6-chloroguanine derivative prepared in Preparation 12 was reacted according to the same procedure as Example 5 to give the title compound.

$^1$H NMR (MeOH-d4) δ 0.68 (t, 1H), 1.13 (m, 1H), 1.21 (d, 3H), 1.42 (t, 1H), 3.84 (t, 1H), 3.97 (t, 1H), 4.40 (d, 1H), 4.66 (d, 1H), 8.63 (s, 1H), 8.73 (s, 1H)

ESI: 314 (M+1)$^+$, C11H16N5O4P

The compound of the present invention exhibits a potent pharmacological effect to a hepatitis B cell line, HepG2.2.15, and a transgenic mouse, widely used for development of a therapeutic agent against hepatitis B, when intravenously or orally administered. The experimental procedures and results are described below.

Experiment 1

Measurement and Analysis of Inhibition Effect Against Hepatitis B Virus (HBV)

(1) Cell Culture and Treatment with Drugs

HepG2.2.15 cell (M. A Shells et al., P.N.A.S. 84, 1005 (1987)), a hepatocarcinoma cell line producing hepatitis B virus, was cultured in DMEM medium (GIBCO BRL, #430-2200) containing 10% FBS (Fetus bovine serum, GIBCO BRL, #16000-044), 1% ABAM (Antibiotic-Antimycotic, GIBCO BRL, #16000-028) and 400 µg/ml of geneticin (Sigma, #G-9516) in a T-75 flask under the conditions of 5% $CO_2$ incubator and 37° C. by dividing in a ratio of 1:3 at an interval of 3 days. The cells were distributed into a 96-well plate in the amount of 4×10$^4$/well and then when 80-90% of cell density was achieved, the old medium was changed with 200 µl of DMEM medium containing 2% FBS, 1% ABAM and 400 µg/ml of geneticin. The drug solution was sequentially diluted five-fold each time, from 100 M to 0.16 M. In order to minimize an experimental error, each treatment was repeated 2-3 times for the respective drugs. The medium was changed every two days. On 10 days after the treatment with drug, 100 µl of the medium was collected and the degree of inhibition of viral replication by drugs was determined through quantitative PCR (Polymerase Chain Reaction).

(2) Determination of Cytotoxicity

After 100 µl of the medium was collected on 10th day from the treatment with drug, 7.5 mg/ml of MTT (Thiazolyl Blue Tetrazolium Broide, Amresco, #0793-5G) solution was added to each well in the amount of 30 µl/well and each cell was cultured for 2 hours in a 5% $CO_2$ incubator at 37° C. The solution was discarded, and an isopropanol solution containing 10% Triton X-100 and 0.4 µl of c-HCl was added to each well in the amount of 120 µl/well. The cells thus dyed were transferred to the isopropanol solution by shaking for 2 hours. Absorbance at 540 nm was measured by Elisa Reader.

(3) PCR Estimation of Inhibition Effect on Hepatitis B Virus Replication

The degree of inhibition by drugs on the replication of hepatitis B virus was determined using the cell culture solution collected on 10th day after the treatment with the drug. The cell culture solution treated with each drug was diluted ten-fold with distilled water and subjected to a pretreatment to destroy the cells by heating them for 15 minutes at 95° C. For the PCR amplification of the gene fragment of about 320 bp, the 2001-base position that is conserved in all sub-strain of hepatitis B virus and 2319-base position that is between the core antigen gene and polymerase gene were used as 5'-end and 3'-end primer, respectively. Then, the amount of genomic DNA of hepatitis B virus was quantified, and the inhibitory effect by drugs on the replication of hepatitis B virus was determined on the basis thereof.

First, the cell culture solution of hepatitis B virus that was not treated with drug was sequentially diluted and amplified through the PCR. The amplified DNA was subjected to electrophoresis on 2% agarose gel and stained with ethidium bromide (EtBr) to be analyzed by IS-1000 (Innotech Scientific Corporation) Digital Imaging System. Analysis of the cell culture solution treated with drug was then carried out using the dilution fold in the range where linearity is maintained. The DNA obtained from the group treated with drug was amplified through the same PCR method, subjected to electrophoresis on 2% agarose gel, stained with ethidium bromide, and analyzed by IS-1000. The degree of inhibition by drugs in the viral replication was quantified by calculating the ratio of test group to control group. Table 8 summarizes the inhibitory effect (pharmaceutical activity and toxicity) of the typical compounds of the present invention.

TABLE 8

| COM. NO. | $EC_{50}$ (µM) in HBV |
| --- | --- |
| PMEA (Comparative Compound) | 5.0 |
| 1 | >1.0 |
| 3 | >0.5 |
| 5 | >0.1 |
| 10 | >0.08 |
| 95 | >0.5 |
| 97 | >0.05 |

As can be seen from the results of Table 8, the compound according to the present invention exhibits 4 to 10-fold greater activity than the comparative compound PMEA that is on Phase III in clinical trials.

Experiment 2

Pharmacological Test on Transgenic Mouse (T/G Mouse)

The compounds were administered via subcutaneous and oral routes in the following animal test.

The test compounds were administered to 4-5 weeks old HBV transgenic mice, which were obtained from FVB strain mice according to a method described in a reference (see, Jone D. Morrey, Kevin W. Bailey, Brent E. Korba, Robert W. Sidwell, "Utilization of transgenic mice replicating high levels of hepatitis B virus for antiviral evaluation of lamivudine" Antiviral research, 1999, 42, 97-108), subcutaneously for 9 days in the amount of 10 mg/kg/day and orally for 9 days in the amount of 10, 2 and 0.4 mg/kg/day, once a day, respectively (the same number of males and females were used). Blood was collected from the tail of the mouse and 5 µl of serum was obtained. To this serum was added 15 ml of Genereleaser sol, which was then pretreated in different temperatures. HBV DNA was taken from the pretreated solution. The DNA was amplified by the PCR (Polymerase Chain Reaction) in the presence of 4 µl of 10× buffer (Perkin Elmer), 0.8 µl of 10 mM dNTP, 500 ng of the same HBV primers as used in Experiment 1, 2,125 mM of $MgCl_2$, DMSO and Taq polymerase. The amount of HBV DNA was analyzed by electrophoresis in order to evaluate a pharmacological effect of the compound of the present invention. The results are described in the following Table 9. In the following Table 9, [mice showing pharmacological effect] means the mice whose blood does not contain HBV DNA.

TABLE 9

| COM. NO. | Amount (mg/kg/day) | Result* | Administration |
|---|---|---|---|
| 23 | 10 | 4/4 | subcutaneous |
| 66 | 10 | 4/4 | subcutaneous |
| 97 | 10 | 4/4 | subcutaneous |
| 95 | 10 | 3/4 | subcutaneous |
| 98 | 10 | 4/4 | subcutaneous |
| PMEA dipivoxil | 2 | 1/3 | oral |
| PMEA dipivoxil | 0.4 | 1/6 | oral |
| 10 | 2 | 4/4 | oral |
| 10 | 0.4 | 5/6 | oral |

*The result means [number of mice showing pharmacological effect/number of total mice]

As can be seen in the above Table 9, the compound of the present invention shows a potent hepatitis B therapeutic effect in the tested animals when orally or subcutaneously administered. Particularly, since the compound of the present invention is superior to the comparative compound PMEA, which is on Phase III in clinical trials, it is expected that the compound of the present invention may be used very effectively for the treatment of hepatitis B.

The invention claimed is:

1. A phosphonate compound represented by the following formula (2):

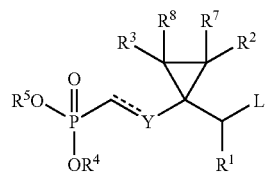

(2)

in which

----- represents single bond or double bond, $R^1$, $R^2$, $R^3$, $R^7$, and $R^8$ independently of one another represent hydrogen, halogen, hydroxyl, amino, $C_1$-$C_7$-alkyl, $C_2$-$C_6$-alkenyl, $C_1$-$C_5$-alkylamino, $C_1$-$C_5$-aminoalkyl, or $C_1$-$C_5$-alkoxy, $R^4$ and $R^5$ independently of one another represent hydrogen, or represent $C_1$-$C_4$-alkyl optionally substituted by one or more substituents selected from the group consisting of halogen, $C_1$-$C_4$-alkoxy, phenoxy, $C_7$-$C_{10}$-phenylalkoxy and $C_2$-$C_5$-acyloxy, wherein $C_2$-$C_5$-acyloxy is RC(O)O— and R is $C_2$-$C_5$-alkyl, or represent $C_1$-$C_7$-acyl, wherein $C_1$-$C_7$-acyl is RC(O)— and R is $C_1$-$C_7$-alkyl, $C_6$-$C_{12}$-aryl or optionally substituted carbamoyl, or represent —(CH$_2$)m-OC(=O)—$R^6$ wherein m denotes an integer of 1 to 12 and $R^6$ represents $C_1$-$C_{12}$-alkyl, $C_2$-$C_7$-alkenyl, $C_1$-$C_5$-alkoxy, $C_1$-$C_7$-alkylamino, di($C_1$-$C_7$-alkyl)amino, $C_3$-$C_6$-cycloalkyl, or 3 to 6-membered heterocycle having 1 or 2 hetero atoms selected from a group consisting of nitrogen and oxygen, Y represents —O—, —S—, —CH(Z)—, =C(Z)—, —N(Z)—, =N—, —SiH(Z)—, or =Si(Z)—, wherein Z represents hydrogen, hydroxyl or halogen, or represents $C_1$-$C_7$-alkyl, $C_1$-$C_5$-alkoxy, allyl, hydroxy-$C_1$-$C_7$-alkyl, $C_1$-$C_7$-aminoalkyl or phenyl, and L represents a leaving group.

* * * * *